(12) United States Patent
Baker et al.

(10) Patent No.: US 8,338,165 B2
(45) Date of Patent: *Dec. 25, 2012

(54) NANOPARTICULATE CELL CULTURE SURFACE

(75) Inventors: Wendy A. Baker, Bath, NY (US); Bertrand De Lambert, Brunoy (FR); David Henry, Morigny-Champigny (FR); Odessa N. Petzold, Elmira, NY (US)

(73) Assignee: Corning Incorporated, Corning, NY (US)

(*) Notice: Subject to any disclaimer, the term of this patent is extended or adjusted under 35 U.S.C. 154(b) by 259 days.

This patent is subject to a terminal disclaimer.

(21) Appl. No.: 12/626,277

(22) Filed: Nov. 25, 2009

(65) Prior Publication Data

US 2010/0159499 A1  Jun. 24, 2010

(30) Foreign Application Priority Data

Nov. 26, 2008 (EP) .................................. 08305846

(51) Int. Cl.
*C12Q 1/02* (2006.01)
*C12P 1/00* (2006.01)
*C12M 1/00* (2006.01)
*C12M 3/00* (2006.01)

(52) U.S. Cl. ......... 435/287.9; 435/29; 435/41; 435/325; 435/283.1

(58) Field of Classification Search ................... None
See application file for complete search history.

(56) References Cited

U.S. PATENT DOCUMENTS

| | | | |
|---|---|---|---|
| 4,877,830 A | 10/1989 | Dobeli et al. | 525/54.3 |
| 5,436,161 A | 7/1995 | Bergstrom et al. | 435/291 |
| 5,620,850 A | 4/1997 | Bamdad et al. | 530/300 |
| 6,884,628 B2 | 4/2005 | Hubbell et al. | 436/518 |
| 2006/0014232 A1 | 1/2006 | Inagawa et al. | 435/23 |
| 2006/0110594 A1 | 5/2006 | Frutos et al. | |
| 2006/0194343 A1 | 8/2006 | Martin et al. | 436/518 |
| 2007/0154348 A1 | 7/2007 | Frutos et al. | 422/57 |

FOREIGN PATENT DOCUMENTS

| | | |
|---|---|---|
| EP | 0226470 | 12/1986 |
| EP | 0253303 | 7/1987 |
| WO | WO2004/046724 | 6/2004 |
| WO | WO2007/049269 | 5/2007 |
| WO | WO2007/078873 | 7/2007 |

OTHER PUBLICATIONS

Abad et al., "Functionalization of Thioacetic Acid—Capped Nanoparticles for Specific Immobilization of Histidine Tagged Proteins", J. Am. Chem. Soc., 2005, 127, 5689-5694.

Gershon PD, Khilko S, "Stable chelating linkage for reversible immobilization of oligohistidine tagged proteins in the Biacore surface plasmon resonance detector", Journal of Immunological Methods, 1995, 183, 65-76 (Abstract only).

Jiang W, Graham B, Spiccia L, Hearn MTW, "Protein selectivity with immobilized Metal Ion-tacn Sorbents: Chromatography Studies with Human Serum Proteins and Several Other Globular Proteins", Anal. Biochem., 1998, 255, 47-58.

S. Lofas, et al., "A Novel Hydrogel Matrix on Gold Surfaces in Surface Plasmon Resonance Sensors for Fast and Efficient Covalent Immobilization of Ligands," J. Chem. Soc., Chem. Commun., 1990, 21, 1526-1528.

Porath J, et al., "Metal chelate affinity chromatography, a new approach to protein fractionation", Nature 1975, 258, 598.

Sigal GB, et al., "A Self-Assembled Monolayer for the Binding and Study of Histidine-Tagged Proteins by Surface Plasmon resonance", Anal. Chem., 1996, 68, 490-497.

Wear M.A., et al., "A surface plasmon resonance-based assay for small molecule inhibitors of human cyclophilin A", Anal. Biochem., 2005, 345, 214-226.

Willard F.S., Siderovski D.P., "Covalent immobilization of histidine-tagged proteins for surface plasmon resonance", Anal. Biochem., 2006, 353, 147-149.

Xu et al., "Nitrilotriacetic Acid-Modified Magnetic Nanoparticles as a General Agent to Bind Histidine Tagged Proteins", J. Am. Chem. Soc., 2004, 126, 3392-3393.

*Primary Examiner* — Amber D Steele
*Assistant Examiner* — Lianko Garyu
(74) *Attorney, Agent, or Firm* — Susan S. Wilks

(57) ABSTRACT

A cell culture article including a substrate having nanoparticles on the substrate surface, the nanoparticle including:

a polymer of formula (I)

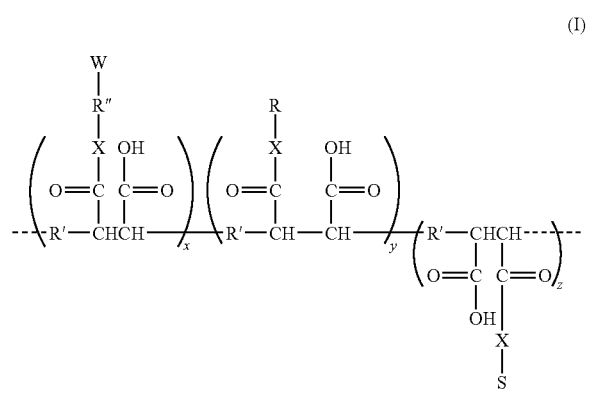

where (x), (y), (z), R, R', R", S, W, and X, are as defined herein. Methods for making the cell culture article or cell culture article and methods for performing an assay of a ligand with the article are also disclosed.

10 Claims, 22 Drawing Sheets

⊢—⊣
1μm

100 μm

100 μm

NANOPARTICULATE CELL CULTURE SURFACE

CROSS-REFERENCE TO RELATED CO-PENDING APPLICATIONS

This application claims the benefit of European Application Serial No. 08305846.1, filed Nov. 26, 2008, entitled NANOPARTICULATE AFFINITY CAPTURE FOR LABEL INDEPENDENT DETECTION SYSTEM and is related to co-pending U.S. patent application Ser. No. 12/620,100, filed Nov. 17, 2009 having the same title. The entire disclosure of publications, patents, and patent documents mentioned herein are incorporated by reference.

BACKGROUND

The disclosure generally relates to surfaces for cell culture, and more particularly to surface chemistry for cell culture in the presence of and absence of serum in cell culture media.

SUMMARY

The disclosure provides surface treated articles for cell culture, and methods for their preparation and use. The cell culture surfaces provide substrates for the culture of cells in the presence of and absence of serum as well as properties amenable for biosensors for label independent detection (LID) and high efficiency biosensors such as Epic® biosensors, resonant grating and like sensing applications. The disclosure also concerns systems and methods providing sensors capable of immobilizing bioentities (e.g., receptor proteins, and like cellular targets) at high density and providing superior sensitivity with respect to detecting an analyte than previously reported. The LID biosensors of the disclosure have higher sensitivity for the detection of bio-molecular recognition events. The treated biosensor surfaces of the disclosure can exhibit increased ligand binding, consume less protein, and provide greater sensitivity compared to known treated biosensor surfaces. The treated biosensor surfaces of the disclosure are also suitable for cell culture.

DETAILED DESCRIPTION

Figure 1A:
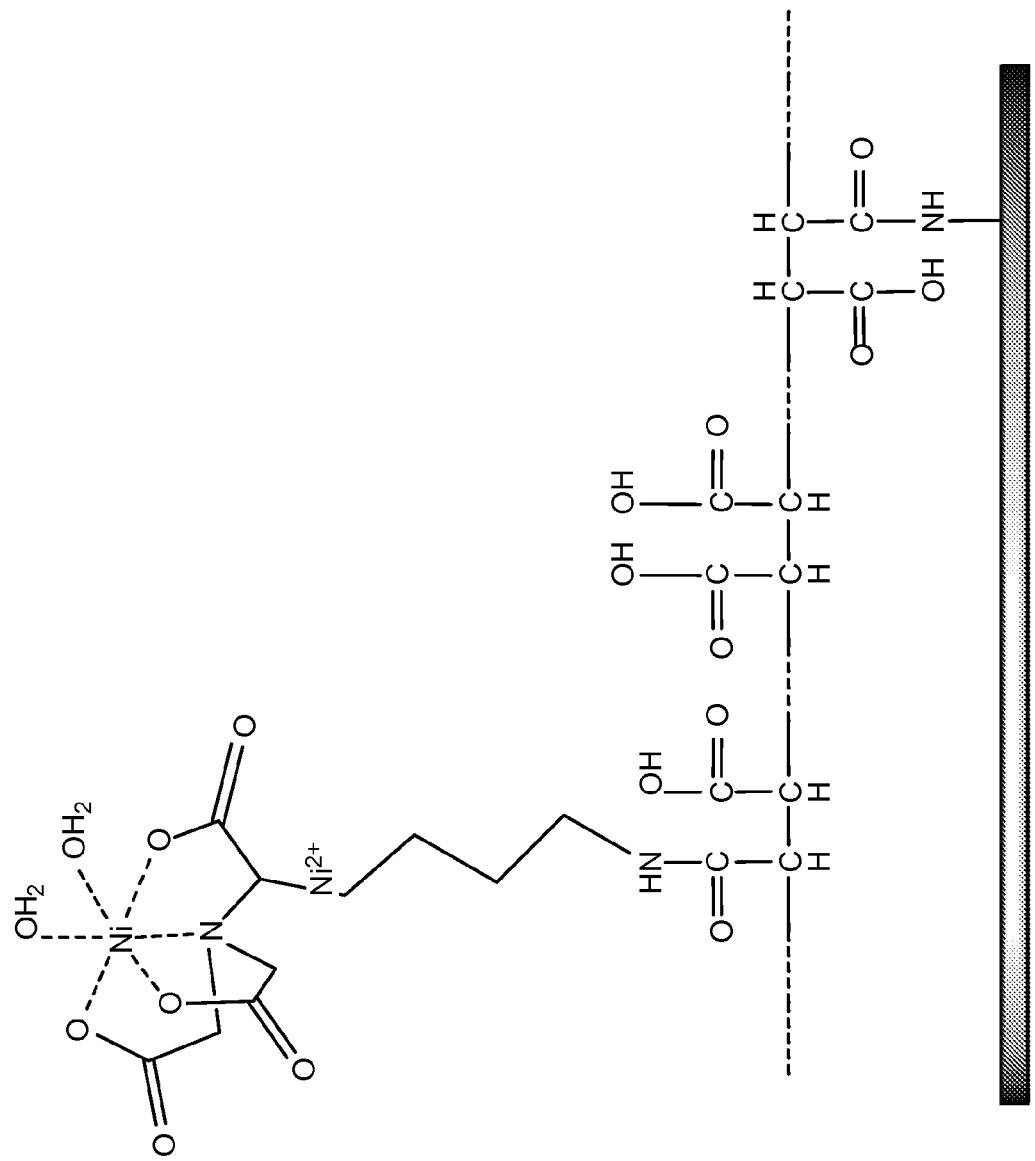
FIGS. 1A-C show exemplary polymer formulas comprising nanoparticles and there function in affinity capture, in embodiments of the disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments for the claimed invention.

DEFINITIONS

"Assay," "assaying," or like terms refers to an analysis to determine, for example, the presence, absence, quantity, extent, kinetics, dynamics, or type of a biologic's or cell's optical or bioimpedance response upon stimulation with an exogenous stimuli, such as a ligand candidate compound, a viral particle, a pathogen, a surface or culture condition, or like entity. Such terms can also include non-biologic or non-cell responses to stimuli or reactions to stimuli.

"Attach," "attachment," "adhere," "adhered," "adherent," "immobilized," or like terms generally refer to immobilizing or fixing, for example, a surface modifier substance, a compatibilizer, a cell, a ligand candidate compound, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting with a cell anchoring material, or like entity.

"Adherent cells" refers to a cell or a cell line or a cell system, such as a prokaryotic or eukaryotic cell, that remains associated with, immobilized on, or in certain contact with the outer surface of a substrate. Such type of cells after culturing can withstand or survive washing and medium exchanging process, a process that is prerequisite to many cell-based assays. "Weakly adherent cells" refers to a cell, a cell line, or a cell system, such as a prokaryotic or eukaryotic cell, which weakly interacts, associates with, or contacts the surface of a substrate during cell culture. However, these types of cells, for example, human embryonic kidney (HEK) cells, tend to dissociate easily from the surface of a substrate by physically disturbing approaches, such as washing or medium exchange. "Suspension cells" refer to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" can also refer to the culturing of cells derived from multicellular eukaryotes, especially animal cells, including the culturing of complex tissues and organs.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of more than one type of cells (or differentiated forms of a single type of cell), which interact with each other, thus performing a biological or physiological or pathophysiological function. Such cell system include, for example, an organ, a tissue, a stem cell, a differentiated hepatocyte cell, or like systems.

"Stimulus," "therapeutic candidate compound," "therapeutic candidate," "prophylactic candidate," "prophylactic agent," "ligand candidate," "ligand," or like terms refer to a molecule or material, naturally occurring or synthetic, which is of interest for its potential to interact with a cell attached to the biosensor or a pathogen. A therapeutic or prophylactic candidate can include, for example, a chemical compound, a biological molecule, a peptide, a protein, a biological sample, a drug candidate small molecule having, for example, a molecular weight of less than about 1,000 Daltons, a drug candidate biologic molecule, a drug candidate small molecule-biologic conjugate, and like materials or molecular entity, or combinations thereof, which can specifically bind to or interact with at least one of a cellular target or a pathogen target such as a protein, DNA, RNA, an ion, a lipid, or like structure or component of a live-cell.

"Biosensor" or like terms generally refer to a device for the detection of an analyte that combines a biological component with a physicochemical detector component. The biosensor typically consists of three parts: a biological component or element (such as a cellular target, tissue, microorganism, pathogen, live-cell, or a combination thereof), a detector element (operating in a physicochemical manner such as optical, piezoelectric, electrochemical, thermometric, or magnetic), and a transducer associated with both components. In embodiments, an optical biosensor can comprise an optical transducer for converting a molecular recognition or molecular stimulation event in a cellular target, a live-cell, a pathogen, or a combination thereof into a quantifiable signal.

"Include," "includes," or like terms refers to including but not limited to, that is, inclusive and not exclusive.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, concentrates, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto are intended to include equivalents of these quantities with or without the "about" modifier.

"Optional," "optionally," or like terms refer to the subsequently described event or circumstance can or cannot occur, and that the description includes instances where the event or circumstance occurs and instances where it does not. For example, the phrase "optional component" means that the component can or can not be present and that the disclosure includes both embodiments including and excluding the component.

"Consisting essentially of" in embodiments refers, for example, to a surface composition, a method of making or using a surface composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agent, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, excessively thick layers of the chelating polymer either as a surface layer, as nanoparticulates, or a combination thereof, such as greater than about 1,000 nm, because of the penetration depth limits of the evanescent wave, and like considerations.

The indefinite article "a" or "an" and its corresponding definite article "the" as used herein means at least one, or one or more, unless specified otherwise.

Abbreviations, which are well known to one of ordinary skill in the art, may be used, for example, "h" or "hr" for hour or hours, "g" or "gm" for gram(s), "mL" for milliliters, "rt" or "RT" for room temperature, "nm" for nanometers, and like abbreviations.

"Weight percent," "wt %," "percent by weight," or like terms with reference to, for example, a component, unless specifically stated to the contrary, refer to the ratio of the weight of the component to the total weight of the composition in which the component is included, expressed as a percentage.

Specific and preferred values disclosed for components, ingredients, additives, cell types, antibodies, His-tagged entities, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

Polymer gels that have been previously described which can immobilize biomolecules on LID biosensors that are made of, for example, a polysaccharide, such as dextran, or a synthetic polymer, such as polyacrylic acid, see, for example, U.S. Pat. No. 5,436,161 (assigned to BIAcore), and EP 0,226,470 patent (the "'470 patent") entitled "Materials and methods for microchemical testing," J. A. Bosley, et al., (assigned to Unilever), Among the numerous types of polymer gels, one frequently used is based on carboxymethyl dextran as described, for example, in S. Lofas, et al., "A Novel Hydrogel Matrix on Gold Surfaces in Surface Plasmon Resonance Sensors for Fast and Efficient Covalent Immobilization of Ligands," *J. Chem. Soc., Chem. Commun.*, 1990, 21, 1526-1528, and the aforementioned U.S. Pat. No. 5,436,161. This carboxymethyl dextran based gel has limited capture capacity due to its molecular weight ($M_w$ 500,000 g/mol for the CM5 sensor chip available from BIAcore) which makes the height or thickness of the final gel unsuitable for very high protein capture capacity.

A similar approach was described in PCT Publication No. WO 2007/049269 (Applicant Bio-Rad). This publication mentions binding layers comprising a polysaccharide substituted with carboxylic acid groups exhibiting high performance in the binding of ligand molecules and in the interaction with analyte molecules. The polysaccharide is modified by reaction with an alanine spacer. This publication mentions that the spacer modification allows more efficient activation of the carboxylic acid groups of the spacer compared to activation of the carboxylic acid groups of a known carboxymethylated polysaccharide. This publication also mentions that synthetic polymers, like poly(acrylic acid) or poly (methacrylic acid), exhibit much more efficient activation and subsequent immobilization. However, the ligand molecules exhibited low activity perhaps due to lower "biocompatibility" of these polymers (see p. 13, lines 5-9).

The LID method is based on the local change of refractive index induced by the adsorption of a ligand onto an immobilized target such as a receptor(s).

The issue of low target immobilization on a biosensor and low specific ligand binding activity on a biosensor can be overcome by the selectively chemically and biologically functionalized surfaces of the disclosure having high biochemical target immobilization on a biosensor and high specific ligand binding activity with the surface bound biochemical target.

The surface disposition of the biosensor article of the disclosure enhances the resulting signal by increasing the immobilized receptor density, i.e., the number of the receptors immobilized on the biosensor which in turn provides increased capture capacity for targeted ligands, and by providing increased activity or availability of the immobilized receptor.

In embodiments, the surface chemistry of the disclosure may be compatible with Dual Polarized Interferometry (DPI), which is another type of LID sensor, or surface plasmon resonance (SPR) type sensors.

In embodiments, the disclosure relates to a method for efficiently immobilizing biomolecules, such as proteins, for example, on a substrate or sensor surface. The disclosure is particularly useful in the field of biosensors for label independent detection (LID). The disclosure relates more particularly to surface chemistry of LID biosensors and a method of preparation.

The disclosure more specifically concerns a sequential method for providing chemically modified surfaces that are capable of immobilizing, for example, receptors (e.g. proteins) by affinity capture at higher density and higher stability than previously reported. The LID biosensor made according to the disclosure has a higher sensitivity for the detection of bio-molecular recognition events compared to known methods. Alternatively or additionally, the immobilization surface does not require any pre-activation, which is otherwise generally time consuming and a source of variability. The disclosure is particularly well suited for LID biosensors, for example, an Epic® system (Corning® Incorporated), those based on surface plasmon resonance (SPR), Dual Polarized Interferometry, and like methodologies.

In the analysis of the biomolecular recognition events with LID, at least one biomolecule must be immobilized on the substrate as close as possible to the wave guide surface and a second molecule partner or complement, which recognizes or is recognized by the immobilized biomolecule, and reacts or binds to the immobilized molecule. Binding locally modifies the refractive index due to the local mass increase and is detected as a wavelength shift or SPR signal.

For LID techniques based on such a local change of refractive index induced by the adsorption of the ligand onto the immobilized receptors, proper surface chemistry can enhance the signal by increasing the number of the receptors immobilized so as to capture a greater amount of ligands. Moreover, the surface chemistry must retain the receptor firmly attached on the sensor surface. Indeed, desorption of the receptor leads to an unacceptable huge variation of the wavelength shift or the SPR signal which may totally hide the binding of the small molecule, such as a new drug entity. To prevent such receptor desorption, covalent attachment of the receptor on the sensor is commonly used. But in some cases, covalent immobilization can lead to partial or complete loss of protein activity, due to random orientation, structural deformation, and like considerations.

To achieve a high binding response, it is desirable to have a high level of immobilized biomolecules, and equally desirable to have immobilized biomolecules available for the binding event. This means that biomolecules must be in a native or active conformation, and well-oriented on the sensor surface to prevent, for example, steric hindrance effects which generally lead to a reduced binding response.

To obtain such biomolecule availability and good orientation, immobilization through affinity capture is generally preferred to covalent attachment. Such affinity capture methods are, for example, based on biotinylated molecules captured by streptavidin or avidin previously attached on the surface, or histidine-tagged molecules captured by a metal ion previously immobilized on the surface. Both of these methods require the addition of a tag to the biomolecule for the immobilization step but can provide excellent availability and good orientation of the immobilized biomolecules. However, for immobilized histidine tagged molecules, desorption is usually observed and can hide binding of small molecules.

The disclosure provides a sequential method for providing biosensor surfaces capable of immobilizing receptors (e.g., proteins) by affinity capture at higher density and higher stability than previously reported, followed by a chemical treatment step that leads to covalent attachment of the receptor(s) on the substrate.

Metal chelate affinity chromatography, reported by Porath (J. Porath, et al., "Metal Chelate Affinity Chromatography, A New Approach to Protein Fractionation," Nature, 1975, Vol. 258, pg. 598), is one known technique for fractionation of proteins by chromatography. This technique allows one to selective capture proteins onto a stationary phase previously functionalized with a metal ion/iminodiacetic acid complex.

Hochuli has described a new metal chelate resin made by grafting carboxymethyl lysine (CML) groups, for example, onto a carrier matrix. The nitrilotriacetic acid (NTA) groups grafted to the matrix provide an efficient chelate resin which exhibits a stronger $Ni^{2+}$ attachment compared to the previously reported iminodiacetic acid based resin (see U.S. Pat. No. 4,887,830, Hochuli, et al., "Metal Chelate Resins," European Patent No. EP 0 253 303B1, Hochuli, et al., "Neue Metallchelatharze," and E. Hochuli, et al., J. Chromatogr, 1987, Vol. 411, pgs. 177-184). This nitrilotriacetic acid group can selectively bind proteins and peptides containing neighboring histidine residues. The method of preparing the nitrilotriacetic compound is described in, e.g., U.S. Pat. No. 4,877, 830.

Due to this significant improvement of the metal/chelate complex stability, nitrilotriacetic acid (NTA)/histidine-tag (HT) technology has become a powerful tool for isolation and purification of recombinant proteins and enzymes modified at their N- or C-termini with histidine residues (K. Terpe, et al., Microbiol. Biotechnol 2003, Vol. 60, pgs. 523-533).

Despite that the NTA/metal/HT interaction is suitable for protein purification, applications requiring longer-term stability such as biosensors, surface coatings, and binding studies are compromised by problems related to metal leaching and protein dissociation (see, e.g., W. Jiang, et al., "Protein Selectivity with Immobilized Metal Ion-tacn Sorbents: Chromatography Studies with Human Serum Proteins and Several Other Globular Proteins," Anal. Biochem., 1998, Vol. 255, pgs. 47-58, and Mateo, et al., Biotechnol. Bioeng., 2001, Vol. 49, pgs. 313-334). The immobilization of the His-tagged protein to the $Ni^{2+}$/NTA surface needs to be stable especially if the kinetics of interactions between immobilized proteins and a further partner, such as a drug are, for example, low. It is known that the stability of the metal ion to NTA is high due to the very high affinity of the metal to the NTA group as demonstrated by Hochuli.

Unfortunately, the histidine tag (His-tag) binds with only low affinity on the metal ion. Nieba estimate the dissociation constant to about $10^{-6}$ M at neutral pH (see L. Nieba, et al., "Biacore Analysis of Histidine—Tagged Proteins Using a Chelating NTA Sensor Chip," Anal. Biochem., 1997, Vol. 252, pgs. 217-228). While this is acceptable for protein purification by immobilized metal ion-affinity chromatography (IMAC), it is less well suited for immobilization on sensors and particularly LID sensors. For these reasons and in spite of its numerous advantages, the NTA capture approach is rarely used for ligand screening using LID, because it is known (see e.g., Gershon, infra.) to cause substantial error in binding responses due to the inevitable protein dissociation.

The present disclosure, in embodiments, provides surface chemistry based on NTA capture but provides further improvements, which for example prevents protein dissociation.

However, despite the risk of protein dissociation, Whitesides, et al., (see, e.g., G. B. Sigal, et al., "A Self-Assembled Monolayer for the Binding and Study of Histidine-Tagged Proteins by Surface Plasmon Resonance," Anal. Chem., 1996, Vol. 68, pgs. 490-497, and U.S. Pat. No. 5,620,850, Whitesides, et al., "Molecular Recognition at Surfaces Derivatized with Self-Assembled Monolayers") described the use of NTA chemistry on SPR sensors for protein capture and analysis of protein/protein interactions. Whiteside, et al., mentioned that this method offers numerous advantages over methods that historically have been used for immobilizing proteins on gold surfaces, including covalent attachment to a carboxylated dextran layer. Indeed, this surface chemistry allows immobilization of protein containing His-tag with a higher percentage of protein recognizable by antibodies and others proteins than can be achieved by covalent modification.

Unfortunately, Whiteside's paper again shows that the protein is more recognizable when immobilized by means of NTA capture chemistry due to the well controlled protein orientation. However, the amount of protein immobilized remains too low for LID application. Whitesides reported that its self-assembled monolayer (SAM) functionalized with the NTA yields to about 1 ng/mm$^2$ of proteins captured (about 1,000 RU immobilization response). Although such a low quantity of immobilized protein is acceptable for large molecule interaction assays such as protein/antibody or protein/ protein assays, it is unsuitable for small molecule/protein assays such as drug/protein assays. The poor immobilization performances of NTA chemistry prepared according to known processes, makes the NTA capture chemistry unsuitable for drug discovery using LID sensors.

Additionally, the problem of low immobilization capacity of an NTA monolayer has been studied by Gershon (P. D. Gershon, et al., "Stable Chelating Linkage for Reversible Immobilization of Oligohistidine Tagged Proteins in the Biacore Surface Plasmon Resonance Detector," Journal of Immunological Methods, 1995, Vol. 183, pgs. 65-76), who proposed an SPR chip coated with NTA modified dextran hydrogel. This chemistry is now commercially available from BIAcore under the trade name NTA-chip. The dextran matrix provides a 3D hydrogel (typically 100 nm thick) which allows capturing significantly much more protein than observed with surface chemistry based on an NTA monolayer (SAM) described above. Although this NTA sensor chip is particularly useful for large molecule interaction studies, it remains unsuitable for small molecule interactions due to the limited amount of immobilized proteins and to high protein dissociation.

To overcome the drawback of protein leaching, another strategy has described how to combine affinity capture and covalent coupling to ensure good protein stability and prevent protein dissociation, see WO 2004/046724; U.S. Patent Publication No. US2006/0014232, to Inagawa, et al., "Immobilization Method"; and F. S. Willard, et al., "Covalent Immobilization of Histidine-Tagged Proteins for Surface Plasmon Resonance," Anal. Biochem., 2006, Vol. 353, pgs. 147-149. Unfortunately, this method suffers from an important drawback: as covalent coupling and affinity capture are realized at the same time, protein attachments are performed in an uncontrolled manner by reaction between reactive groups of the surface and reactive groups from the proteins without any specificity. This is particularly unsuitable because the main reason to select capture of protein by affinity is that the protein is attached to the sensor surface by means of only the tag having a well defined position and not by a non-specific chemical reaction. Another strategy was applied using the NTA-chip. After immobilization of proteins on the NTA-chip, an EDC/NHS treatment was performed on immobilized biomolecules to create covalent bonds between the substrate and the biomolecules (see M. A. Wear, et al., "A Surface Plasmon Resonance-Based Assay for Small Molecule Inhibitors of Human Cyclophilin A," Anal. Biochem., 2005, Vol. 345, pgs. 214-226). Unfortunately, even if no dissociation of biomolecules from the substrate was observed after the EDC/NHS treatment, protein leaching appears to be important during the activation step. Coupled with the inherently poor immobilization capacity of the chemistry of known methods, protein leaching or loss from the surface further contributes to a decrease in the amount of immobilized protein on the substrate. Finally, the low capacity of biomolecules captured appears to be a primary drawback that prevents this chemistry from being suitable for small molecule recognition events.

Attempts to attach NTA chelating groups on metal nanoparticles such as gold-nanoparticles (see Abad, et al., "Functionalization of Thioacetic Acid-Capped Nanoparticles for Specific Immobilization of Histidine Tagged Proteins," J. Am. Chem. Soc., 2005, Vol. 127, pgs. 5689-5694) or magnetic-nanoparticles (see Xu, et al., "Nitrilotriacetic Acid-Modified Magnetic Nanoparticles as a General Agent to Bind Histidine tagged Proteins," J. Am. Chem. Soc., 2004, Vol. 126, pgs. 3392-3393) have been described but they do not mention how to enhance efficiency of LID sensors with polymer only based nanoparticles.

In embodiments, the present disclosure provides affinity based surface chemistry that has, for example, a very high immobilization capacity, which is compatible with label free detection, which provides a high stability NTA-Ni-histidine complex, and which prevents substantially any protein dissociation using a post-immobilization covalent attachment reaction prior to ligand detection.

In embodiments, the disclosure provides a biosensor article comprising:
a substrate having nanoparticles (NP) on the substrate surface, the nanoparticle comprises:
a polymer of formula (I)

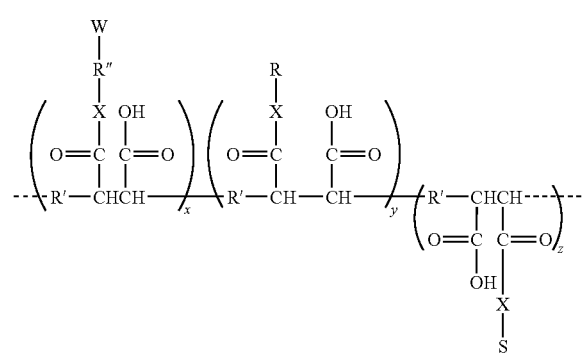

having at least one of: a metal-ion chelating group (x), an ionizable group (y), and a surface substantive group (z), where R is hydrogen or a substituted or unsubstituted, linear or branched, monovalent hydrocarbyl moiety having from 1 to 6 carbon atoms;

R' is a substituted or unsubstituted, linear or branched, divalent hydrocarbyl moiety resulting from copolymerization of an unsaturated monomer having from 2 to 10 carbon atoms with, for example, maleic anhydride;

R" is a substituted or unsubstituted, linear or branched, divalent hydrocarbyl moiety having from 1 to 10 carbon atoms;

S comprises at least one point of attachment to a substrate, and can be, for example, a substrate surface group or modified surface group that can covalently bond to the polymer via the X substituent;

W comprises at least one metal-ion chelate groups, and is an incipient binding site for a biomolecule having at least one tag, that is W can be, for example, at least one bi-dentate group, such as a metal-ion chelating group in the absence of a metal-ion, and can be, for example, an active binding site for a biomolecule having at least one tag in the presence of a chelated metal ion.

X can be, for example, —NH—, —NR—, or O, and like divalent groups;

the mole ratio of x:(y+z) groups can be, for example, from about 2:8 to about 8:2; and the nanoparticles can have, for example, a diameter of from about 10 to about 100 nanometers.

In embodiments, the disclosure provides a cell culture article comprising:
a substrate having nanoparticles (NP) on the substrate surface, the nanoparticle comprises:
a polymer of formula (I)

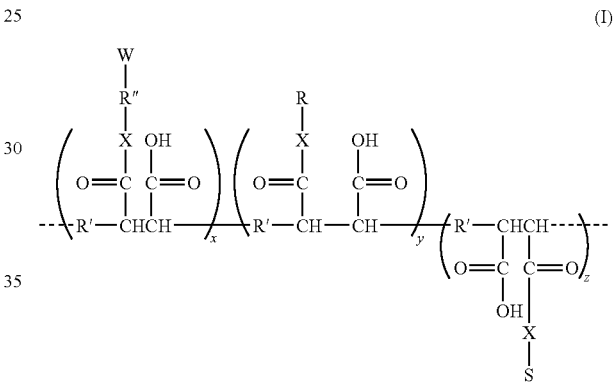

having at least one of: a metal-ion chelating group (x), an ionizable group (y), and a surface substantive group (z), where R is hydrogen or a substituted or unsubstituted, linear or branched, monovalent hydrocarbyl moiety having from 1 to 6 carbon atoms;

R' is a substituted or unsubstituted, linear or branched, divalent hydrocarbyl moiety resulting from copolymerization of an unsaturated monomer having from 2 to 18 carbon atoms with maleic anhydride;

R" is a substituted or unsubstituted, linear or branched, divalent hydrocarbyl moiety having from 1 to 20 carbon atoms;

S comprises at least one point of attachment to the substrate;

W comprises at least one bi-dentate group;

X is an —NH—, —NR—, or O;

the mole ratio of x:(y+z) groups is from about 2:8 to about 8:2; and the nanoparticles have a diameter of from about 10 to about 100 nanometers.

In embodiments, R is a hydroxy substituted, monovalent hydrocarbyl moiety having from 2 to 6 carbon atoms.

In embodiments, the mole ratio x:(y+z) is about 1:1.

In embodiments, S comprises at least one of: a metal oxide, a mixed metal oxide, a polymer, a composite, or a combination thereof; a surface modified substrate; or a combination thereof.

In embodiments, R is a hydroxy substituted alkyl having from 2 to 4 carbon atoms; R' is a divalent hydrocarbyl moiety having from 2 to 10 carbon atoms; R" is a substituted or unsubstituted, divalent hydrocarbyl moiety having from 3 to 6 carbon atoms; S is an aminosiloxane treated glass or plastic substrate; W comprises at least one iminodiacetic acid, nitrilotriacetic acid, triazacyclononane, aminoethylethanolamine, triethylenetetramine, 2-hydroxypropane-1,2,3-tricarboxylate, or a mixture thereof; X is —NH—; the mole ratio x:(y+z) is from about 2:1 to about 1:2; and the nanoparticles have a diameter of from about 10 to about 100 nanometers.

In embodiments, R is a hydroxy substituted alkyl having from 2 to 4 carbon atoms; R' is a divalent hydrocarbyl moiety having from 2 to 10 carbon atoms;

R" is a substituted or unsubstituted, divalent hydrocarbyl moiety having from 3 to 6 carbon atoms; S is a plastic substrate; W comprises nitrilotriacetic acid; X is —NH—;

the mole ratio x:(y+z) is from about 2:1 to about 1:2; and the nanoparticles have a diameter of from about 10 to about 100 nanometers.

In embodiments, the disclosure provides a method of culturing cells comprising:

providing a cell culture substrate as described; providing cells to the cell culture substrate; incubating the cells in a suitable media on the cell culture substrate. In embodiments, the disclosure provides providing a sandwich layer to the cells on the cell culture substrate in the presence of or absence of serum. In embodiments, the cells are hepatocytes.

In embodiments, the R group in (y) can be, for example, a hydroxy substituted, monovalent hydrocarbyl moiety having from 2 to 6 carbon atoms, for example, the product of the polymer, for example having residual anhydride groups, and ethanol amine. In embodiments, R can be, for example, hydrogen, or a hydroxy substituted, linear or branched alkyl having from 2 to 4 carbon atoms, such as ethylene, propylene, butylene, and like substituted hydrocarbyl moieties.

In embodiments, the R' can be, for example, a divalent hydrocarbyl moiety having from 2 to 10 carbon atoms. R' can be, for example, ethylene, propylene, isobutylene, styrene, and like hydrocarbyl moieties, see for example, PCT/US2006/047885, at page 12.

In embodiments, the R" can be, for example, a substituted or unsubstituted, divalent hydrocarbyl moiety having from 3 to 6 carbon atoms.

In embodiments, the S can be, for example, at least one of: a metal oxide, a mixed metal oxide, a polymer, a composite, or a combination thereof, for example, $Nb_2O_5$, $SiO_2$, $Nb_2O_5$/$SiO_2$, cyclic olefin copolymer, and like points of attachment to a substrate. S can be, for example, an aminosiloxane treated glass or plastic substrate. The S can additionally or alternatively be, for example, a surface coating modified substrate, such as with known silanes GAPS, APS, MOPS, and like modifiers, or a combination thereof.

In embodiments, the W chelating group can be, for example, at least one iminodiacetic acid (IDA), nitrilotriacetic acid (NTA), triazacyclononane (TACN), aminoethylethanolamine, triethylenetetramine, 2-hydroxypropane-1,2,3-tricarboxylate (citrate), and like bis-, tris-, and multi-dentate chelating substituents, derivatives thereof, or a combination thereof. The metal-chelate group can be mono-NTA, bis-NTA or tris-NTA, tetrakis-NTA, poly-NTA, and like groups, or a combination thereof. The ionizable groups can be, for example, carboxylic acid groups, and like groups, or a combination thereof.

In embodiments, the X can be, for example, —NH— (an auric-acid), —O— (a hemi-ester), and like groups, or a combination thereof. In embodiments, a preferred X is —NH—.

In embodiments, the mole ratio x:(y+z) can be, for example, from about 2:8 to about 8:2; from about 2:1 to about 1:2; and from about 1 to about 1, including all intermediate values and ranges. The mole ratio of x:(y+z) can preferably be, for example, about 1:1, such as found in the exemplary EMA050NTA material disclosed herein.

In embodiments, the nanoparticles (NP) on the substrate surface can be, for example, a layer of nanoparticles, polymer film, or a combination of nanoparticles and polymer film. The polymeric nanoparticle layer can be, for example, a coat or coating of nanoparticles, by analogy for example with "a coating of dust or snow (particles)" and which layer or coating can have, for example, complete or incomplete substrate surface coverage. The nanoparticles can have a particle diameter thickness of, for example, from about 10 to about 1,000 nanometers, from about 20 to about 1,000 nanometers, from about 20 to about 500 nanometers, from about 20 to about 300 nanometers, from about 20 to about 200 nanometers, from about 20 to about 150 nanometers, from about 20 to about 100 nanometers, from about 20 to about 75 nanometers, and like particle diameter thickness, including all intermediate ranges and values. In embodiments, the nanoparticles can have a diameter of, for example, from about 10 to about 100 nanometers, from about 10 to about 60 nanometers and from about 20 to about 40 nanometers, including all intermediate ranges and values.

A brief summary of one illustrative preparative procedure for making a biosensor article includes, for example, coating a suitable substrate, such as an insert or glass slide with a tie-layer or conversion coating, such as obtained by treatment with APS. Next, the tie-layer treated substrate can be, for example, dip-coated in a solution or dispersion of the polymer, such as an EMA050NTA solution at a concentration of 1 mg/mL in DMSO:IPA=50/50=v:v, over about 10 min. The rinsed and dried polymer coated substrate is then treated with ethanolamine or like agent, either neat or in a suitable solution such as a borate buffer, for about 30 min. The metal ion can be complexed with the polymer by, for example, the addition of a suitable metal salt solution, such as 40 mM $NiSO_4$ solution, and stirring for about 30 min.

In embodiments, the polymer can be, for example, a pre-formed derivatized product of a maleic anhydride (MA) polymer or ethylene-maleic anhydride (EMA) copolymer having a portion of the backbone derivatized with a spacer (R"), at least one bi-dentate group such as a metal-ion chelator (W), and optionally a metal-ion ($M^{n+}$). In embodiments, the polymer can alternatively be prepared, for example, by contacting the nanoparticle decorated substrate surface and a compound having a spacer and a metal chelator (e.g., carboxymethyl lysine; CML also known as NTA), and then contacting the nanoparticle decorated substrate having the attached spacer and a bi-dentate metal-ion chelator, and a metal-ion solution to form nanoparticles having at least some chelated metal ion.

Figure 1B:
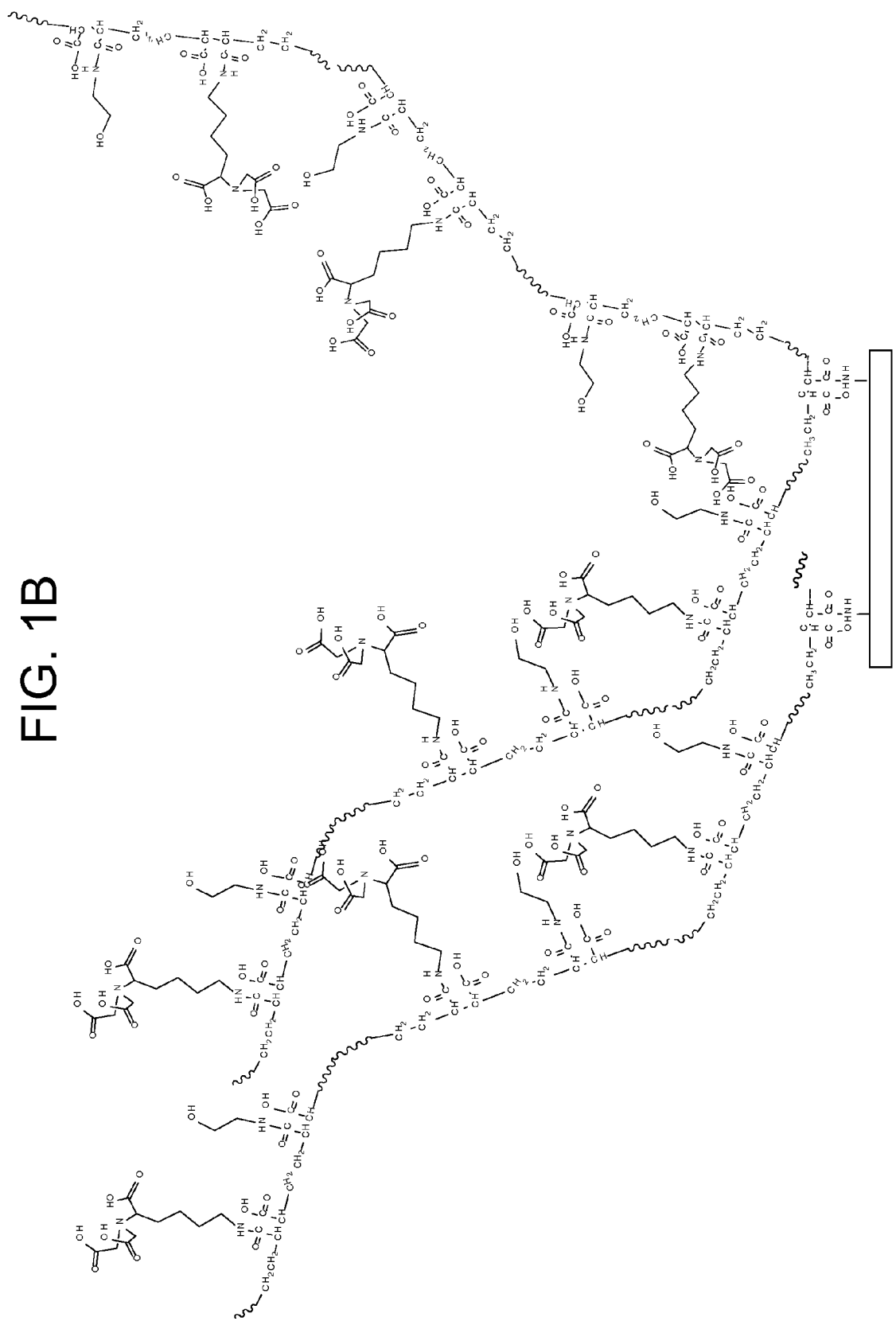

FIG. 1B shows an exemplary structure of the polymer of formula (I) associated with a surface (S). Although not limited by theory, it is believed that nanoparticles of the polymer of formula (I) can reversibly relax or unfold in certain solutions, such as buffer media, to provide an extended structure more akin to sea-weed attached to the bottom of lake by a single or very few points of attachment. The extended structure can provide a greater number of points where the metal ion may complex and thus where a tagged biomolecule or like entity can complex.

In embodiments, the disclosure provides a method for using the disclosed biosensor article comprising:

contacting the substrate having the abovementioned metal-ion complexed nanoparticles (NP) and a His-tagged entity target, such as a small molecule, Ab, protein, cell, and like entities, having at least one His-tag or label, for example, His-tagged carbonic anhydrase, to immobilize the His-tagged entity, and contacting the nanoparticles having the immobilized His-tagged entity and a stabilizing agent to form a nanoparticle decorated substrate having a stabilized His-tagged entity.

Figure 1C:
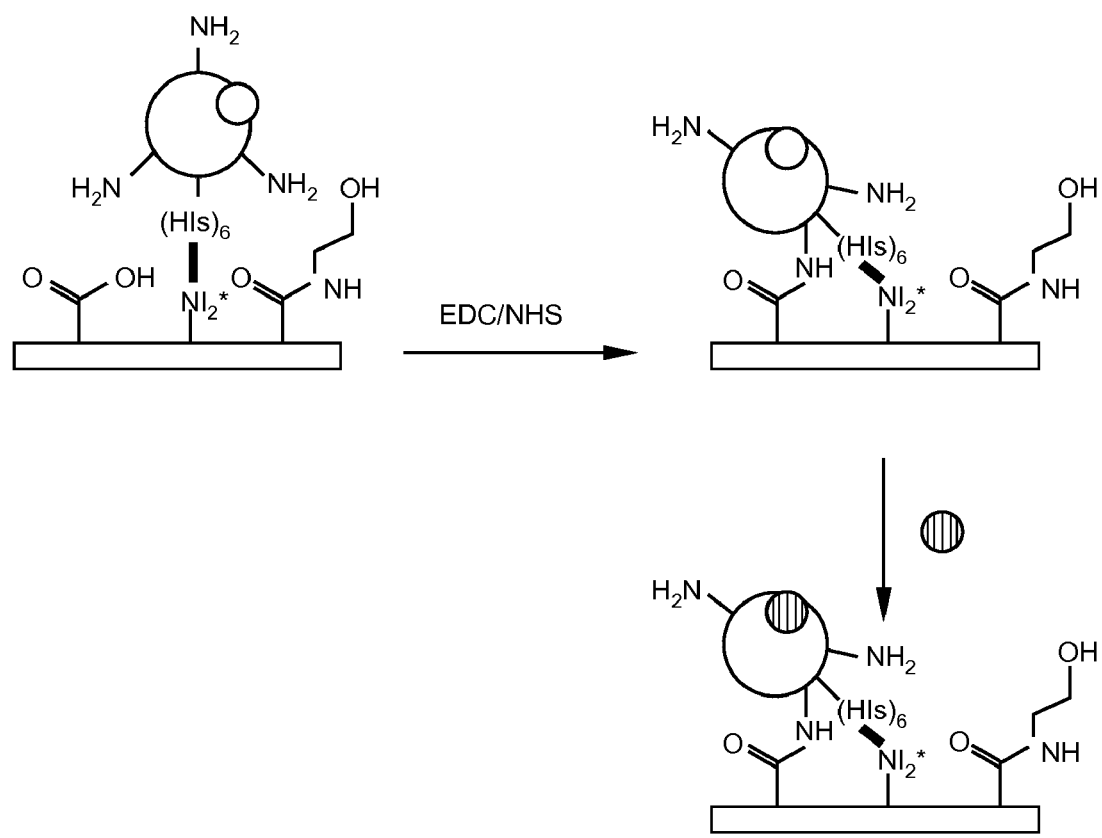

The stabilizing agent can be, for example, NHS/EDC, and like reagents or treatments. The stabilized intermediate product resulting from the contacting with the stabilizing agent need not be isolated. If desired, stabilized intermediate product can be used directly in covalent ligand capture and sensing. The method of use can further include contacting the nanoparticle decorated substrate having the stabilized His-tagged entity, with a ligand to form a nanoparticle decorated substrate having a His-tagged entity having a bound ligand, i.e., a ligand for the His-tagged entity or His-tag conjugate-former, e.g., small molecule, Ab, protein, cell, and like ligands. The His-tag target affinity capture, the stabilization step, and the covalent ligand capture and sensing are schematically illustrated in FIG. 1C.

In embodiments, contacting the nanoparticle decorated substrate with a His-tagged entity, i.e., immobilization, can be accomplished at, for example, a pH of from about 3 to about 9. The contacting of the nanoparticle decorated substrate with a His-tagged entity can be accomplished at, for example, a pH above the pI of the His-tagged entity.

In embodiments, the His-tagged entity immobilization can be, for example, greater than about 1,500 pm and the loss of immobilized His-tagged entity can be, for example, less than about 0.1 wt % of the total originally immobilized His-tagged entity, which increased immobilization and stability properties taken together provide a biosensor having a biosensor binding response greater than about 10 picometers (pm). The biosensor can be, for example, at least one of a surface plasmon resonance biosensor, a waveguide resonant grating biosensor, an impedance biosensor, a mass spectrometry biosensor, and like devices, or a combination thereof.

In embodiments, the disclosure provides a method for performing an assay of a ligand, the method comprising:

contacting the ligand and a biosensor article as disclosed herein, such that if the ligand binds to the His-tagged entity, then: detecting the ligand-induced response of the biosensor.

In embodiments, the His-tagged entity can be, for example, at least one of: a natural or synthetic oligonucleotide, a natural or synthetic nucleic acid (DNA or RNA), a natural peptide, a natural or synthetic peptide optionally comprising one or more modified or blocked amino acids, an antibody, a hapten, a biological ligand, a protein membrane, a lipid membrane, a protein, a small molecule having a molecular weight of less than about 500 Daltons, a cell, or a combination thereof, or a conjugate thereof, where the His-tagged entity has at least one His-tag or His-label, and preferably more than one His-tag or His-label, such as from about two to about six, including intermediate values and ranges.

In embodiments, the ligand can be, for example, at least one of: a stimulus, a therapeutic candidate, a prophylactic candidate, a prophylactic agent, a chemical compound, a biological molecule, a peptide, a protein, a biological sample, a small molecule having a molecular weight of less than about 500 Daltons, a biologic drug molecule candidate, a drug candidate small molecule-biologic conjugate, a pathogen, a cell, or combinations thereof. While the ligand may include a His-tag or His-label, the ligand need not include a His-tag or His-label to be operational in binding or biosensing embodiments of the disclosure.

In embodiments, the disclosure provides a method for using the biosensor article as disclosed herein, including, for example, contacting the nanoparticle decorated substrate having the His-tagged entity and a stabilizing agent to form a nanoparticle decorated substrate having a stabilized His-tagged entity. The method can further include contacting the resulting nanoparticle decorated substrate having a stabilized His-tagged entity and a ligand to form a nanoparticle decorated substrate having the His-tagged entity now having a bound ligand.

In embodiments, the disclosure provides an article prepared by the above method for use in a biosensor or a cell culture.

In embodiments, a polymer of the formula (I) can be, for example, Formula I(a):

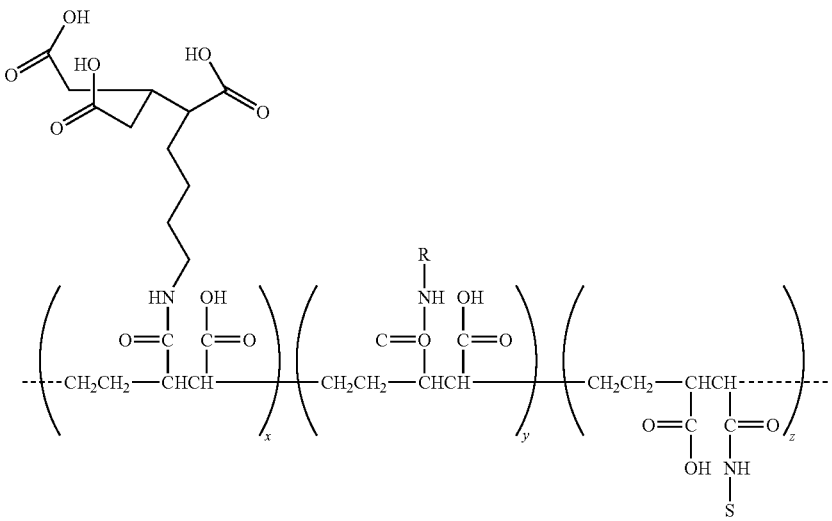

In embodiments, a polymer of the formula (I) can be, for example, of the formula I(b):

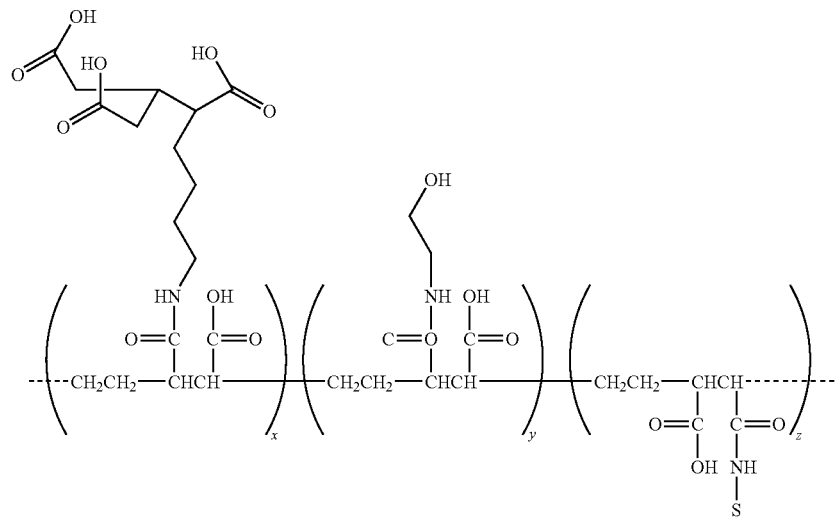

In embodiments, a polymer of the formula (I) when complexed with a metal-ion such as $Ni^{2+}$, can be, for example, of the formula I(c):

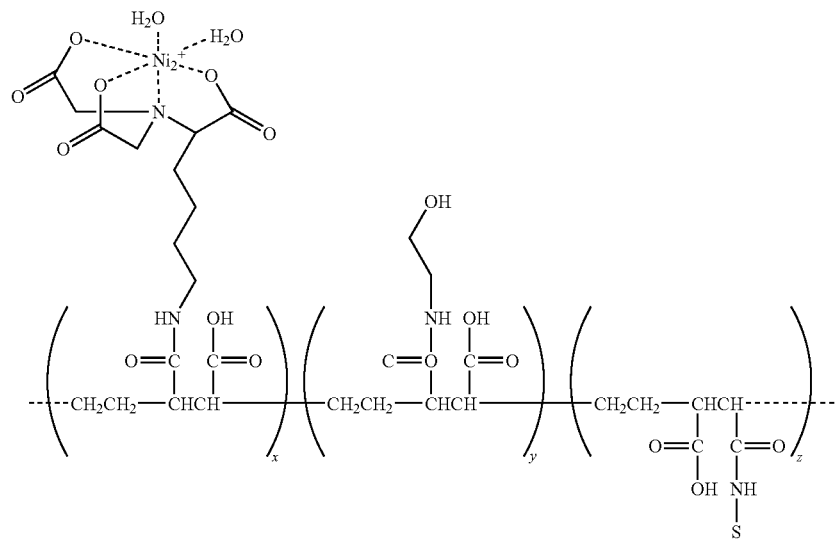

When a LID biosensor such as grating resonant sensors or SPR-sensors are used, the evanescent field wave can only probe about the first 100 to about 200 nanometers from the surface making a micrometer thick gel unsuitable. Thus, biomolecules that have been captured in the gel beyond about 200 nm from the sensor surface are effectively invisible to the evanescent field wave, and any biomolecular recognition event occurring beyond about 200 nm is not detected. This situation yields unacceptably high biomolecule consumption, which further limits it's applicability for high throughput system (HTS) applications, such as those involving precious protein.

In embodiments, the disclosure provides a surface chemistry, based on synthetic polymers, which can be easily attached to a LID sensor surface, has very high immobilization capacity, provides good availability and activity of the immobilized biomolecule, and is compatible with label-free detection methodologies. The method of making is easy to implement, and is compatible with manufacture scale-up, e.g., does not require long polymerization times nor long washing times.

In embodiments, the disclosure provides a surface chemistry, based on synthetic polymers, which can be attached to a substrate suitable for cell culture applications. In embodiments, the surface chemistry is a nanoparticle layer on the surface of a substrate. In embodiments, a substrate suitable for cell culture application may be, for example, glass, metal, ceramic, or polymeric material. Suitable polymeric material may be any substrate known in the art and may include, for example, polyacrylates, polymethylacrylates, polycarbonates, polystyrenes, polysulphones, polyhydroxy acids, polyanhydrides, polyorthoesters, polypropylenes, polyphosphazenes, polyphosphates, polyesters, cyclic polyolefin copolymers or mixtures thereof, which may be surface modified (for example plasma treated) or untreated. In embodiments, suitable cell culture articles include microwell plates, slides, flasks, cell stack or multi-layer cell culture articles such as Corning's HyperFlask™ or HyperStack™ products. In embodiments, the nanoparticle layer on the surface of the substrate is a polymer of Formula I. In embodiments, the nanoparticle layer on the surface of the substrate is Formula I(a) or Formula I(b) where there is no metal chelated to the metal chelating group (x). In embodiments, the nanoparticle layer for cell culture applications is the nanoparticle layer illustrated in FIG. 1B. In embodiments, the cell culture article is suitable for culturing cells including primary cells, for example, human primary hepatocytes, cell lines including, for example, HepG2/C3A (ATCC #CRL-10741, 3-20 passages), HepG2 (ATCC #HB-8065, 3-20 passages), Fa2N-4 (commercially available from XenoTech, passages 32-34), or the like. These cells may be cultured in any suitable media including, for example, media commercially available from XenoTech, Invitrogen or the like.

Experiments comparing four hour attachment of human primary hepatocytes on EMA NTA synthetic surface (as shown in FIG. 1B) relative to collagen I show that the synthetic surface, EMA NTA supports attachment of human primary hepatocytes similar to collagen I in serum culture conditions for four hours. The expression of bile canaliculi and apical domain are physiologically relevant markers for hepatocytes in culture. MRP2 transporter is a marker of the bile canaliculi structures at the apical domain between hepatocytes and indicates the degree of restoration of cell membrane polarity of cells in culture. Extended and networked bile canaliculi structures indicate good (in vivo like) restoration of cell polarity and a more in vivo-like cell morphology. EMA NTA surface shows similar performance to collagen; without the Matrigel™ overlay (sandwich), hepatocyte polarity (in vivo like morphology) is not restored, and with the Matrigel™ overlay (sandwich), hepatocyte polarity (in vivo like morphology) is restored to a relatively greater degree than cells growing on other experimental cell culture surfaces (data not shown). These extended and networked bile canaliculi structures can be seen in FIG. 17 (FIG. 17 illustrates control surfaces) 18 and 19.

Figure 15:
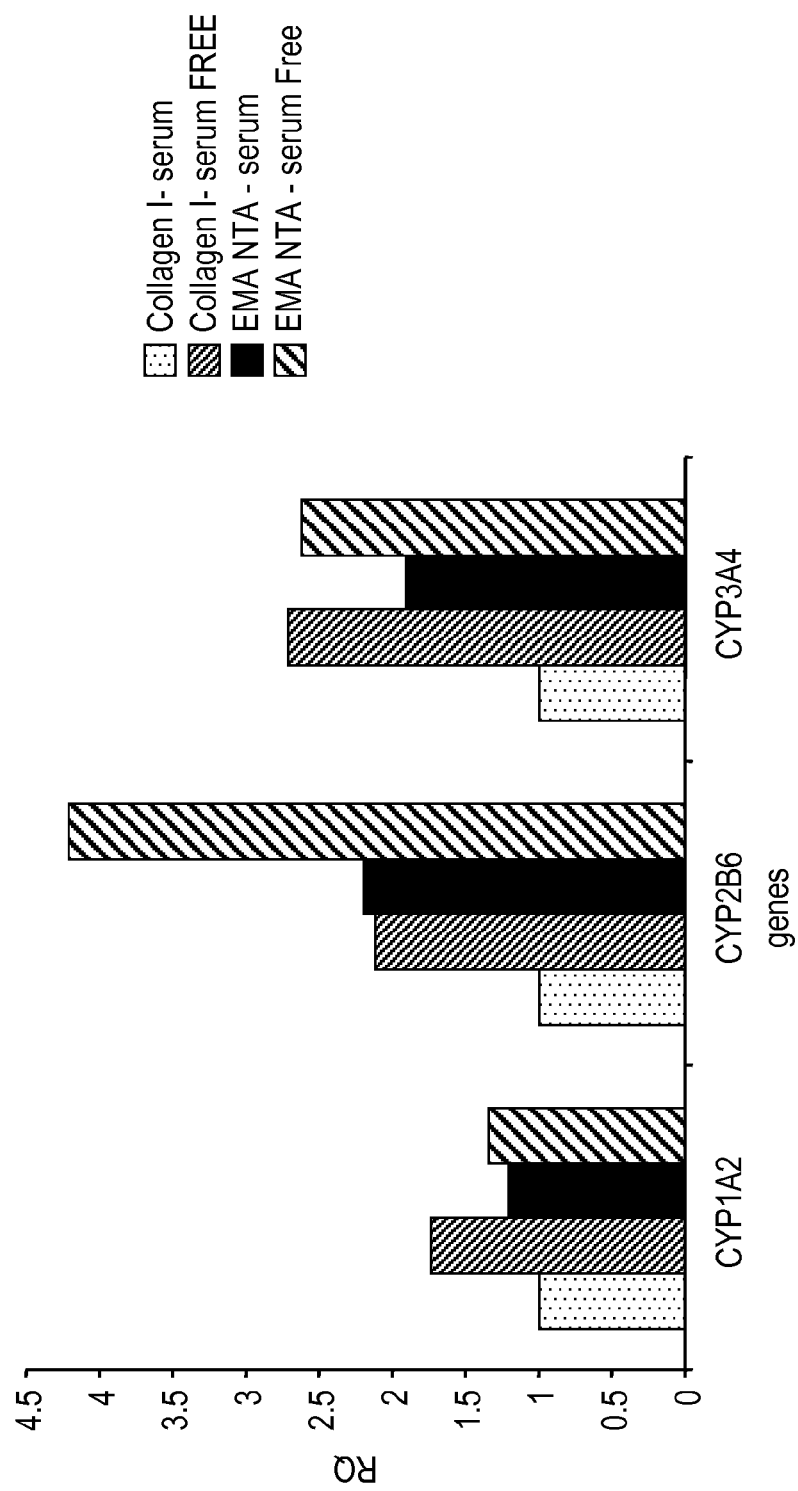
FIG. 15 shows relative gene expression of three major metabolism genes (CYP450) in human primary hepatocytes cultured on EMA NTA synthetic surface relative to collagen I.
Figure 19A:
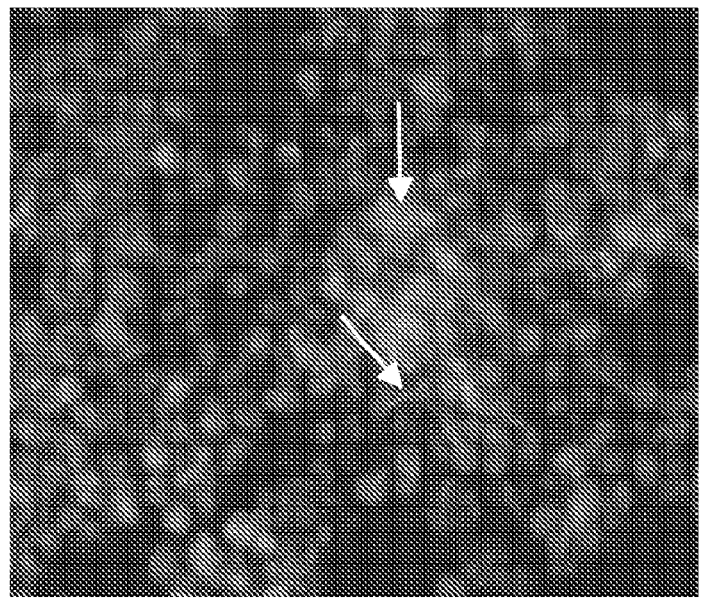
FIGS. 19 (A and B) are micrographs of liver cells grown on synthetic EMA NTA surface in the presence of a Matrigel™ sandwich in the presence of serum (FIG. 19A) and in the absence of serum (FIG. 19B) stained to show MRP2 transporter.
Figure 19B:
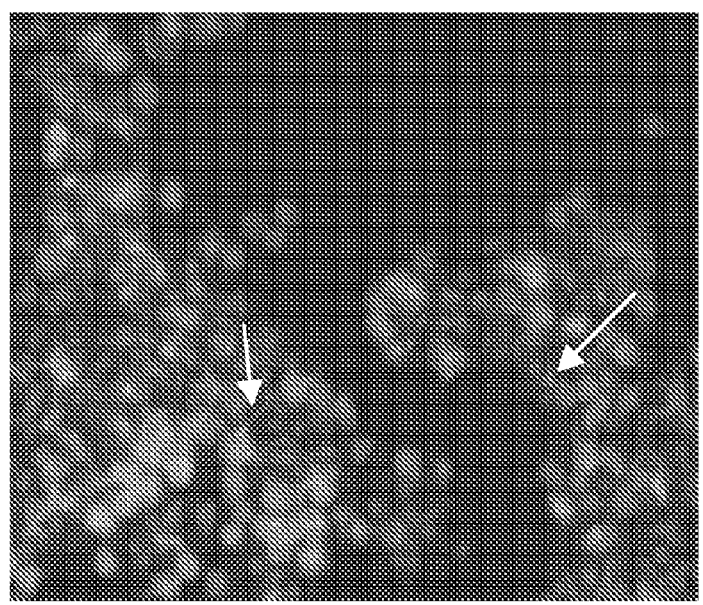

Experiments testing the ability of the EMA NTA surface to support the culture of cells in the presence and absence of serum show that cells are successfully cultured on the EMA NTA surface in the presence and in the absence of serum. For example, FIG. 15 shows that gene expression is distributed more homogeneously across the EMA NTA surfaces in the presence of serum. FIG. 19 shows that there may be more crowding and clustering of cells in the serum free condition (FIG. 19B) than in standard culture conditions with serum (see FIG. 17 and see also FIG. 19A on the EMA NTA surface in the presence of serum). Bile canaliculi structures appear to be further extended and more interconnected in the regions where cells are clustered under serum free culture conditions. This may explain the slight increase in function (gene expression) observed in the serum free conditions (see FIG. 15).

By using the described preparative method, a very reproducible nanoparticle layer on the surface of the substrate can be obtained which is fully compatible with commercially available LID systems such as the Epic® system (Corning Incorporated) and with the preparation of cell culture articles.

The nanoparticle layer on the surface of the substrate provides enhanced capture of the biomolecules as demonstrated in the working examples. The nanoparticle layer on the surface of the substrate can be, for example, from about 10 to about 100 nm, as measured by, for example, SEM or AFM methods.

Because a very high immobilization level of protein can be obtained and a high activity of the protein established, the coated sensor article of the disclosure can be particularly suitable for detecting binding events occurring between proteins and very low molecular weight molecules, e.g., small molecules.

Alternative or additional reactive comonomers can be selected which comprise or can be converted after in-situ polymerization to aldehyde, azide, epoxy, isocyanate, isothiocyanate, sulfonyl chloride, carbonate, maleimide, acyl imidazole, aziridine, imidazole carbamate, succinimidyl ester and succinimidyl carbonate, hydrazone, iminodiacetic acid, nitrilo triacetic acid, triazacyclononane, thiol, substituted disulfide group such as pyridine disulfide, and like groups. A panel of reactive groups that can be used with the present disclosure is disclosed, e.g., in "Bioconjugate Techniques", Greg T. Hermanson, Academic Press, 1996. When the reactive group is likely to interfere with the polymerization of the monomers mixture, the reactive group can be, for example, introduced after the in-situ polymerization or can be protected using a protecting group methods.

The present disclosure provides a process for preparing LID sensors having unexpectedly high protein immobilization capacity while significantly improving the protein activity which dramatically enhances the assay sensitivity, as illustrated and demonstrated herein. The immobilization and binding responses of the biosensor articles of the disclosure out-perform other known surface chemistries. For example, the Epic® binding response for a furosemide/carbonic anhydrase assay as disclosed herein, can be, for example, at least about 2 to about 10 times higher than the those obtained with a sensor made according to the method described in WO 2007/078873.

In embodiments, the sensor of the disclosure is compatible with high throughput screening (HTS) of drug or other small molecules due to the high binding response provided. Even very low molecular weight compounds, such as fragments having a molecular weight of less than about 500 Daltons, can be also screened using the sensor due to the high binding response.

In embodiments, the disclosure permits preparation of sensors for label-free detection using a low protein concentration which suggests that the cost per analysis can be substantially reduced compared to other LID techniques.

In embodiments, the disclosure provides a surface that is suitable for the attachment, growth, and assay of many types of cells, including strongly adherent cells such as Chinese hamster ovary (CHO) cells and human epithelial carcinoma A431 cells, intermediate adherent cells such as RMS13 cells, and weakly adherent cells such as human embryonic kidney (HEK) cells, or primary cells.

The disclosure provides methods to modify the surface of a biosensor so that the surface of these biosensors is compatible with and amenable to cell culture and subsequent cell assays. The disclosed method is suitable for oxidized metal thin film surfaces such as the ones used in resonant waveguide grating biosensors, or an un-patterned gold surface, such as those used in surface plasmon resonance (SPR), or a patterned gold surface, such as those used in electrical bioimpedance-based biosensors.

The disclosure may suitably comprise, consist of, or consist essentially of: a cell culture article as defined herein; a method for preparing the cell culture article as defined herein; and a method for performing an assay of a ligand as defined herein. In embodiments, the disclosure provides a cell culture article comprising: a substrate; an optional tie-layer attached to at least the substrate; and a bio-compatible layer of the disclosed polymer attached to the optional tie layer, to the substrate, or both.

The substrate can comprise, for example, a plastic, a polymeric or co-polymeric substance, a ceramic, a glass, a metal, a crystalline material, a noble or semi-noble metal, a metallic or non-metallic oxide, a transition metal, or a combination thereof. In embodiments, the tie-layer can be obtained from a compound comprising one or more reactive functional groups comprising, for example, an amino group, a thiol group, a hydroxyl group, a carboxyl group, an acrylic acid, an organic or inorganic acid, an ester, an anhydride, an aldehyde, an epoxide, and like groups, and salts thereof, or a combination thereof. The choice of materials for forming the tie-layer can depend on the nature of the substrate. For example, silane can be an excellent tie-layer in conjunction with an oxidized inorganic substrate such as glass, $SiO_x$-presenting substrate, $TiO_2$, $Nb_2O_5$, $Ta_2O_5$, $HfO_2$, and mixtures thereof, or like substrate. Alternatively or additionally, the aforementioned inorganic substrates can be combined with a $SiO_x$ overlay. A thiol compound can be an excellent tie-layer when a gold substrate is selected. A positively charged polymer such as poly-lysine can be an excellent tie-layer when a polymeric substrate is used.

In embodiments, the tie layer can be obtained from, for example, a straight or branched-chain aminosilane, aminoalkoxysilane, aminoalkylsilane, aminoarylsilane, aminoaryloxysilane, or like silanes or salt thereof, and combinations thereof. Specific examples of compounds that can be used to form the tie layer include, for example, 3-aminopropyl trimethoxysilane, N-(beta-aminoethyl)-3-aminopropyl trimethoxysilane, N-(beta-aminoethyl)-3-aminopropyl triethoxysilane, N'-(beta-aminoethyl)-3-aminopropyl methoxysilane, aminopropylsilsesquioxane, or like compounds, and combinations thereof. In a preferred embodiment, the tie layer can be, for example, aminopropylsilsesquioxane, the polymer can be, for example, poly(alkylene-co-maleic anhydride), and the substrate can be, for example, a microplate or a microscope slide. In embodiments, the tie layer can be, for example, poly-lysine, polyethyleneimine, and like substantive polymers, or combinations thereof. Pludemann mentions surface modifiers, a silicone elastomer or like rubber applications, such as articles or devices, and like applications, in *Silane Coupling Agents*, (1982). For additional definitions, descriptions, and methods of silica materials and related metal oxide materials, see for example, R. K. Iler, *The Chemistry of Silica*, Wiley-Interscience, 1979.

In embodiments, the bio-compatible nanoparticulate polymer layer can have a thickness, for example, of from about 10 Å to about 2,000 Å, from about 10 Å to about 1,500 Å, from about 10 Å to about 1,250 Å, from about 10 Å to about 1,000 Å, and from about 10 Å to about 100 Å. In embodiments, the polymer layer that forms the bio-compatible layer, if initially continuous, can be ruptured or disrupted during an extended or a vigorous oxidation process to provide bio-compatible layers that includes gaps or regions with little or no coverage of the underlying tie-layer or the substrate surface, that is a discontinuous layer or film of the bio-compatible nanoparticulate polymer layer can result. Similarly, a discontinuous layer or film of the bio-compatible nanoparticulate polymer layer can result from less extensive or less vigorous oxidation of an initially discontinuous polymer layer. Accordingly, the bio-compatible nanoparticulate polymer layer having ruptured areas or a discontinuous layer can have layer thicknesses of, for example, from about 10 to about 200 Å. In embodiments, the nanoparticulate polymer can have a thickness of from about 10 Å to about 2,000 Å before or after complexation with a metal-ion.

The enhancements of the present disclosure are applicable to other substrates including other glasses, metals, plastic substrates, such as Topas® COC substrates, available from TOPAS Advanced Polymers, Inc., and like materials, or a combination thereof. Commonly owned and assigned copending U.S. patent application Ser. No. 12/201,029, filed Aug. 29, 2008, mentions plasma treated cyclic polyolefin copolymer surfaces having enhanced binding density for biologically active agents and cells. These plasma treated cyclic polyolefin copolymer surfaces may be selected as substrates in the present disclosure.

A $Nb_2O_5$ wave guide surface is well suited for biosensor-based cell assays, which can attach cells onto the bare $Nb_2O_5$ or nanoparticulate polymer coated $Nb_2O_5$ biosensor surface, and have the associated cells in close proximity of the detection zone of biosensor systems.

In embodiments, the disclosure provides a sensor and process for label-free detection having metal-chelate surface chemistry comprising a layer having polymer nanoparticles, that is, colloidal polymer particles made of a polymer having both metal chelating groups and ionizable groups. In a second step after biomolecule immobilization, a chemical treatment step creates covalent interactions between the immobilized biomolecules and the biosensor surface, which precludes dissociation.

We have surprisingly discovered that chemistry based on polymer nanoparticles bearing NTA groups and having a second covalent bonding step between immobilized biomolecules and the substrate overcome the known drawbacks by providing a sensor surface having a very high protein immobilization capacity and no protein dissociation, which makes this sensor surface highly compatible with low molecular weight drug screening using LID.

The metal-chelate surface having polymer nanoparticles can be easily prepared by reaction between a maleic anhydride copolymer and a compound bearing the chelating group, for example, the NTA. The NTA-modified maleic anhydride copolymer can be obtained by reaction of the maleic anhydride copolymer and one reactant having at least one NTA group, at least one thiol, at least one hydroxyl group, or at least one amino group, which group can react with the anhydride group leading to the formation of ester, thioester, imide, or amide group, respectively. Preferably, the compound can be selected from compounds described in EP 0253303B1 (Hochuli, et al., "Neue Metallchelatharze"). More preferably the compound is N,N bis-(Carboxymethyl)-L-Lysine, or its salt form such as the N,N bis-(Carboxymethyl)-L-Lysine disodium salt mono hydrate, for example.

The size of the NTA-maleic anhydride nanoparticles are preferably about 5 to about 200 nm. The ratio between NTA groups and ionizable groups of the polymer backbone can be, for example, less than about 1 and greater than about 0.33. Thus, the ratio of NTA:COOH can be about 1:1 to about 1:3.

In a second step, after biomolecule immobilization, treatment with EDC/NHS or like reagents, activates carboxylic groups that create covalent bonds between affinity immobilized biomolecules and the substrate.

Figure 3:
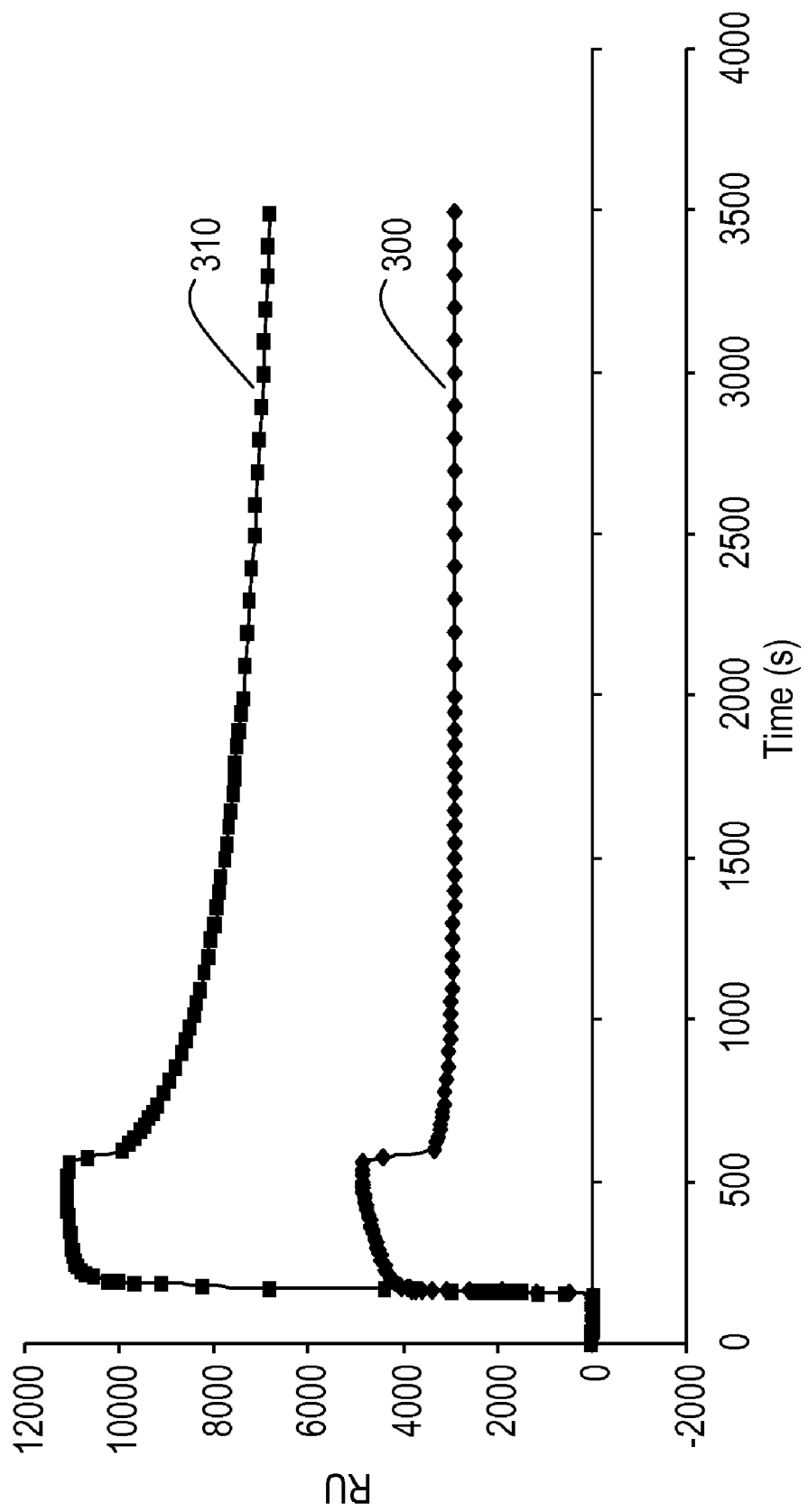
FIG. 3 shows SPR responses for the surfaces with and without nanoparticle texture of Example 2, in embodiments of the disclosure.
Figure 4:
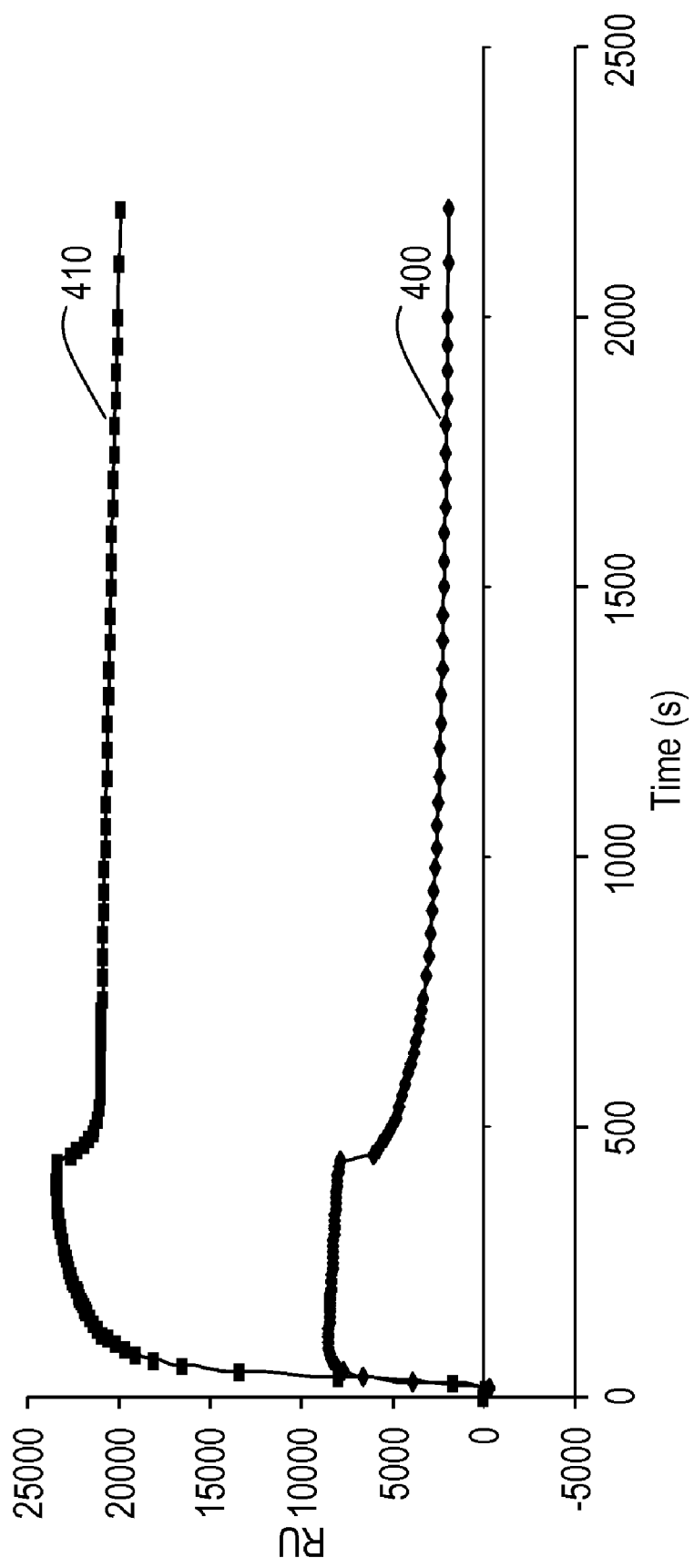
FIG. 4 shows SPR responses using a commercially available NTA chip without nanoparticle texture compared with the present Example 3 with nanoparticle texture, in embodiments of the disclosure.

The disclosure provides an affinity chemistry with very high immobilization capacity, which is important to detecting and observing binding events. The surface chemistry of the disclosure provides a layer of polymer nanoparticles, which provides high protein/target immobilization. In an illustrative embodiment, the polymer EMA050NTA (i.e., an ethylene-maleic anhydride copolymer having about half or 50 mol % of the anhydride moieties derivatized with NTA groups) was coated on a gold chip, either: i) in 100% good solvent leading to 2D surface chemistry (i.e., without particles); or ii) in mixed solvent leading to 3D surface chemistry having nanoparticles. After further addition of the nickel solution to form chelated nickel, proteins immobilization was performed (FIG. 3). SPR responses clearly showed significant improvement, such as greater than about double or more, for the immobilization level when the coating included the polymer nanoparticles. In addition, protein immobilization was made on a Biacore NTA-chip and on a gold chip coated with the nanoparticle layer of the disclosure using the same experimental conditions. SPR responses also indicated very high immobilization levels, such as double or triple the response, on the disclosed surfaces compared to a commercial chip (FIG. 4). In addition, protein leaching appears to be significantly lower on the surfaces of the disclosure compared to Biacore NTA-chip. In embodiments, the disclosed articles and assay processes maintain high protein immobilization even after an activation step with EDC/NHS.

Figure 5:
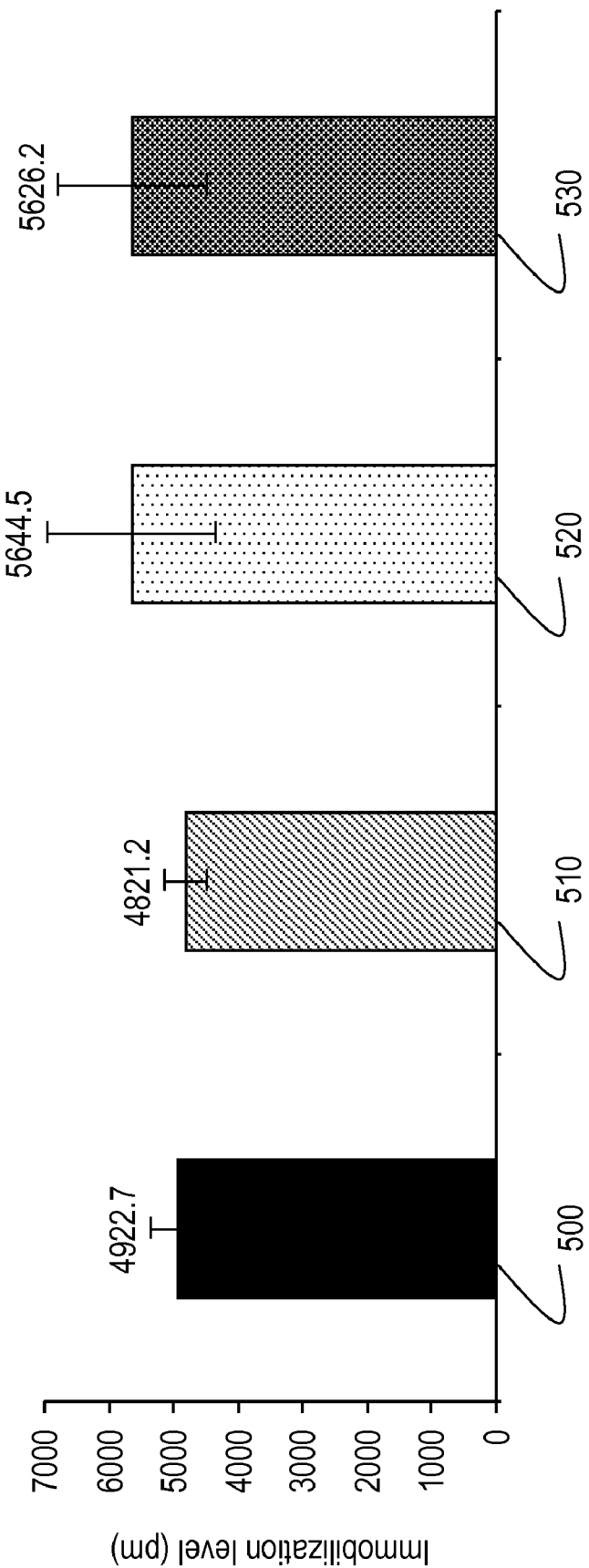
FIG. 5 shows a comparison of His-tag CAR immobilization levels on an affinity surface only and on the affinity/covalent surface of Example 4, in embodiments of the disclosure.

In embodiments, the disclosure prevents protein dissociation using covalent attachment between immobilized target biomolecules and the substrate. In Example 2, his-tag carbonic anhydrase (H) was immobilized on a nanoparticle polymer layer having NTA/Ni-ion complexes. When the EDC/NHS treatment was performed, no protein leaching was observed leading to high binding values with furosemide ligand. Conversely, without EDC/NHS treatment, interactions between proteins and the substrate are based only on affinity interactions and dissociation of the proteins from the surface was observed (FIG. 6), which reversibility is an inherent aspect of affinity methods and consequently has no significant binding values (FIG. 5). In this example, it is important to notice that using a high pH buffer for immobilization, such as whose pH was higher than the pI of the proteins, had no impact on binding results.

Moreover, we have surprisingly discovered that performing the EDC/NHS treatment step is important for best results. In particular, it is important to distinguish methods of literature in which EDC/NHS treatment is applied before protein immobilization and the present immobilization method, which is accomplished in two steps. First, proteins are immobilized on the affinity surface referred to as, for example, EMA050NTA-Ni, and secondly an EDC/NHS treatment is performed on immobilized proteins. Example 3 shows the importance of this second step, as immobilization level and binding results are significantly improved compared to comparative methods (FIGS. 5 and 7, 8 and 10, and 11 and 12).

Figure 9:
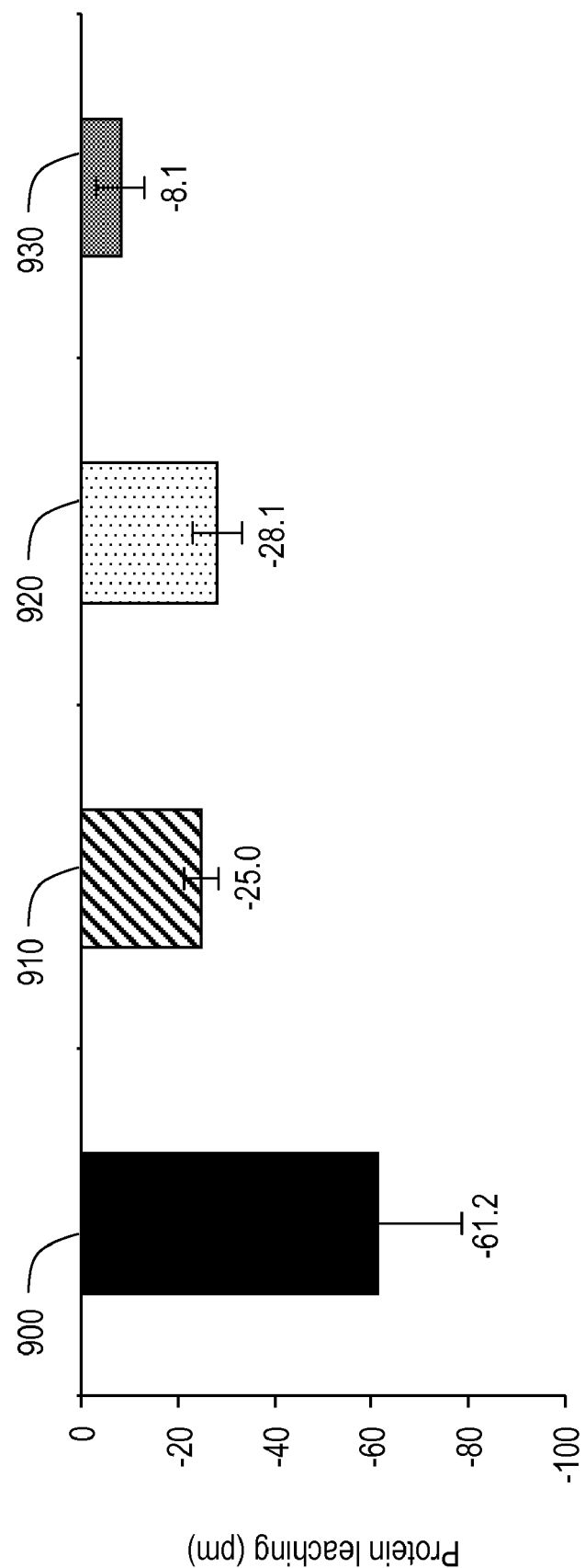
FIG. 9 shows a comparison of protein leaching or dissociation responses on an affinity surface, on affinity/covalent surface of a commercially available product, and on the affinity/covalent surface of Example 5, in embodiments of the disclosure.
Figure 10:
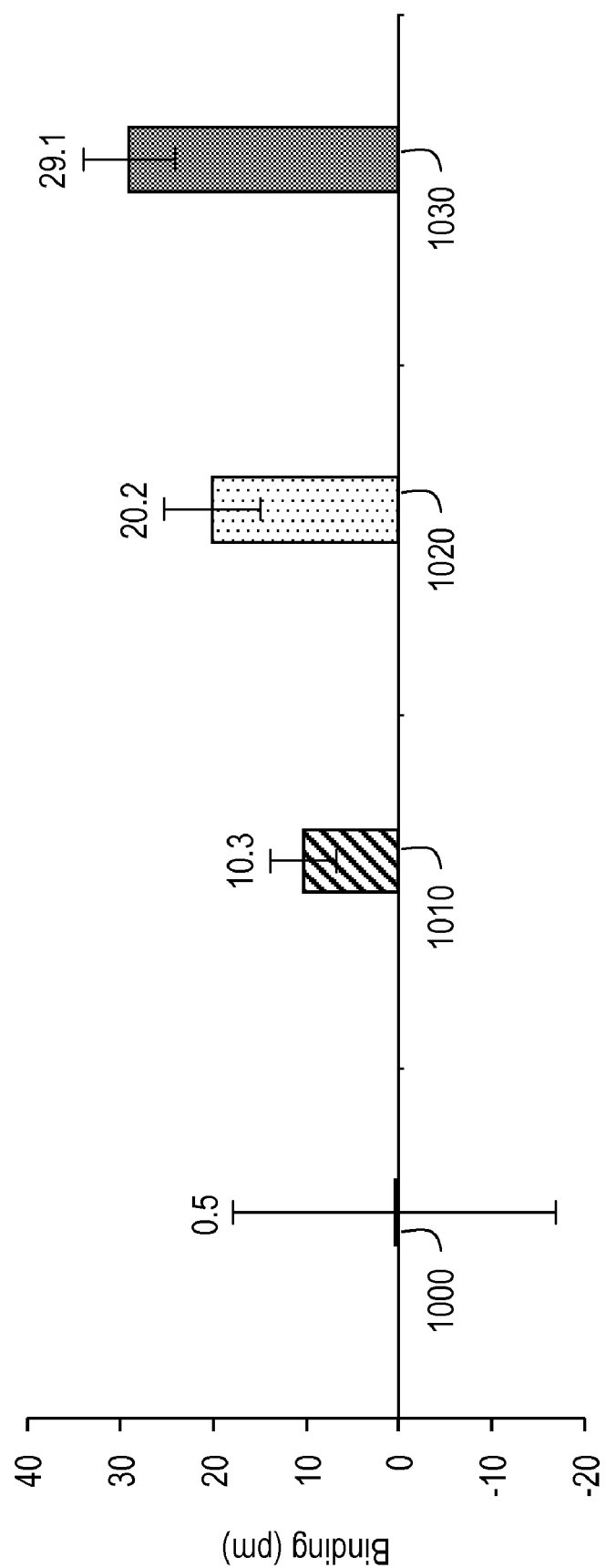
FIG. 10 shows a comparison of binding values on an affinity surface, on an affinity/covalent surface of a commercially available product, and on the affinity/covalent surface of Example 5, in embodiments of the disclosure.

Examples 4 and 5 show a specific aspect of protein immobilization on EMA050NTA-Ni chemistry as no significant immobilization levels were obtained when non-tagged carbonic anhydrase was added on EMA050NTA-Ni surface (FIG. 9), and when histidine-tagged carbonic anhydrase was added on the EMA050NTA surface without nickel treatment (FIG. 10).

In embodiments, the disclosure provides preparative methods for sensors and biosensor surface layers having very high protein immobilization capacity, high observed protein immobilization, and a high binding response.

The disclosed methods and sensors are straight forward and are compatible with any label free detection platform, such as SPR, resonant gratings, Epic® sensor plates, or dual polarization interferometry, and optionally including a micro-fluidic system.

The disclosure provides a method that permits immobilization of proteins over a wide pH, especially at a pH level above the pI of protein target.

Referring to the Figures, FIG. 1A shows a schematic representation of the polymer of formula (I) comprising the nanoparticles. FIG. 1B was described above. FIG. 1C illustrates affinity capture, covalent bonding, and ligand capture steps.

Figure 2A:
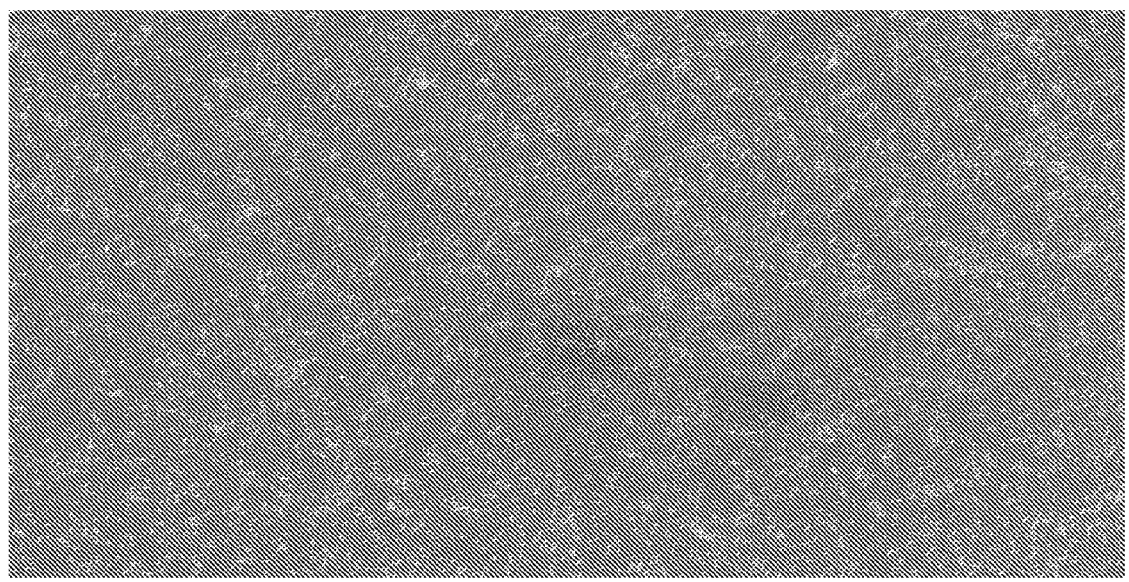
FIGS. 2A-C show SEM images of NTA derivatized EMA nanoparticles, in embodiments of the disclosure.
Figure 2B:
Figure 2C:
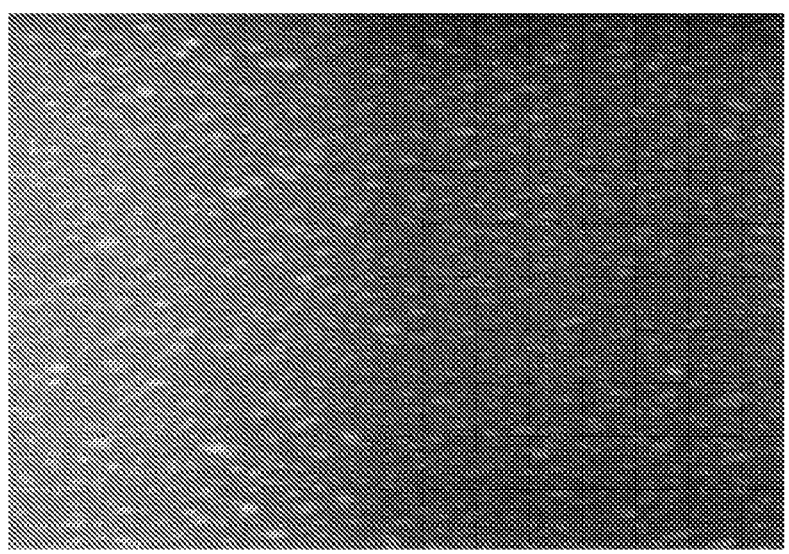

FIG. 2A shows a SEM image of NTA derivatized EMA nanoparticles. FIGS. 2B and 2C show SEM images of EMA050NTA nanoparticles only, and EMA050NTA nanoparticles having been treated with ethanolamine blocking and nickel-ion, respectively.

FIG. 3 shows SPR responses for the surfaces with (310) and without (300) nanoparticle texture of Example 2.

FIG. 4 shows SPR responses using a commercially available NTA chip (400) compared with the present Example 3 (410).

FIG. 5 shows a comparison of His-tag CAII immobilization levels on an affinity surface only (500, 510) and on the affinity/covalent surface of Example 4 (520, 530).

Figure 6:
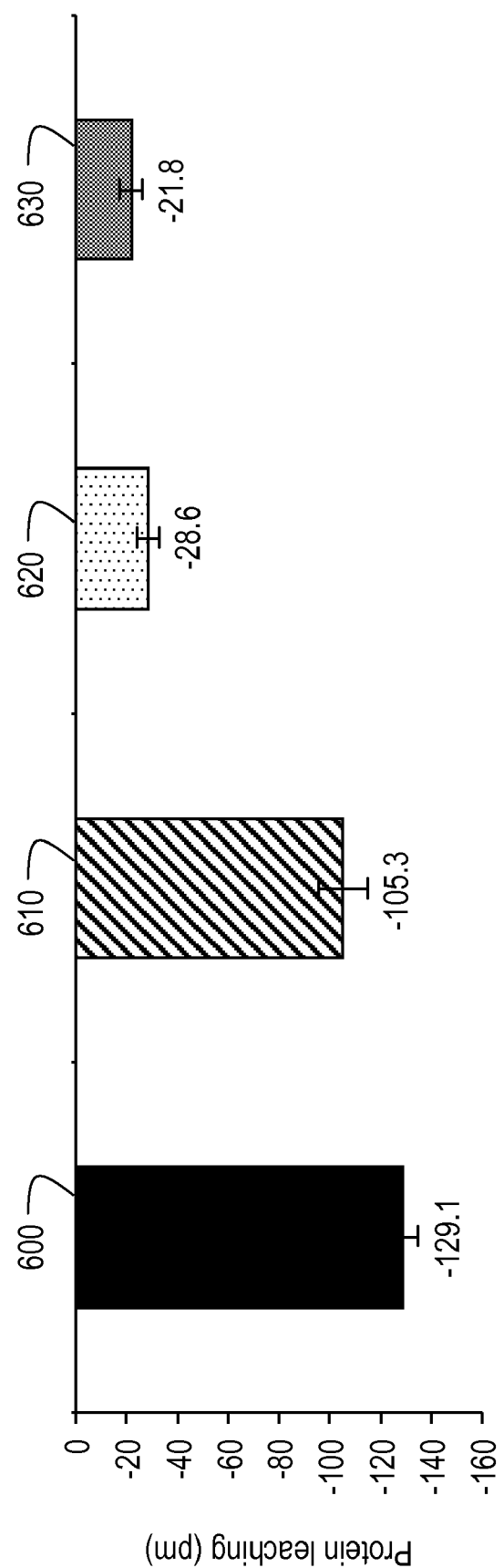
FIG. 6 shows a comparison of protein leaching responses on the affinity surface and the affinity/covalent surface of Example 4, in embodiments of the disclosure.

FIG. 6 shows a comparison of protein leaching responses on the affinity surface (600, 610) and the affinity/covalent surface of Example 4 (620, 630).

Figure 7:
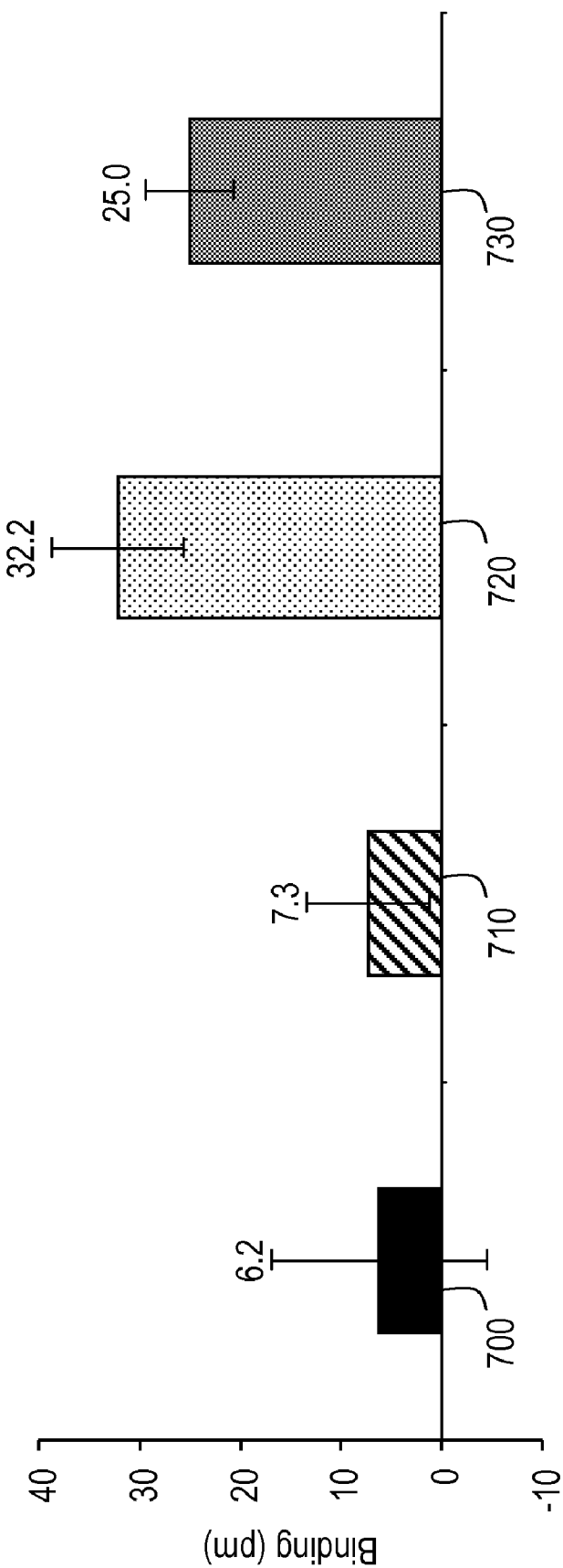
FIG. 7 shows a comparison of binding values on the affinity surface only and on the affinity/covalent surface of Example 4, in embodiments of the disclosure.

FIG. 7 shows a comparison of binding values on the affinity surface only (700, 710) and on the affinity/covalent surface of Example 4 (720, 730).

Figure 8:
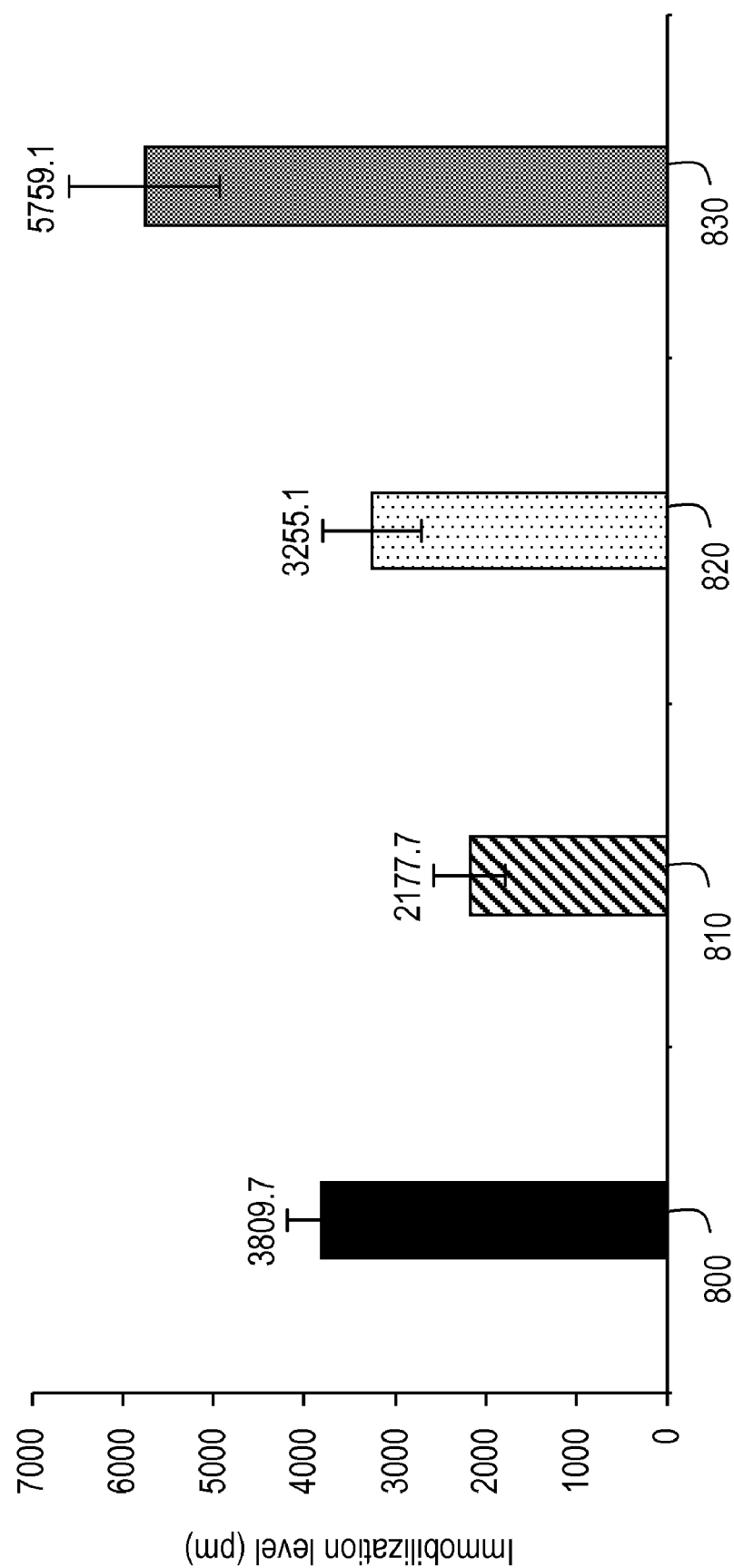
FIG. 8 shows a comparison of His-tag CAII immobilization levels on the affinity surface and on the affinity/covalent surface of a commercially available product and on the affinity/covalent surface of Example 5, in embodiments of the disclosure.

FIG. 8 shows a comparison of His-tag CAII immobilization levels on the affinity surface (800) and on the affinity/covalent surface (810 with $Ni^{2+}$ ion, 820 without $Ni^{2+}$ ion) of a commercially available product and on the affinity/covalent surface of Example 5 (830).

FIG. 9 shows a comparison of protein leaching or dissociation responses on an affinity surface (900), on affinity/covalent surface of a commercially available product (910 with Ni ion, 920 without Ni ion), and on the affinity/covalent surface of Example 5 (930).

FIG. 10 shows a comparison of binding values on an affinity surface (1000), on an affinity/covalent surface of a commercially available product (1010 with Ni ion, 1020 without Ni ion), and on the affinity/covalent surface of Example 5 (1030).

Figure 11:
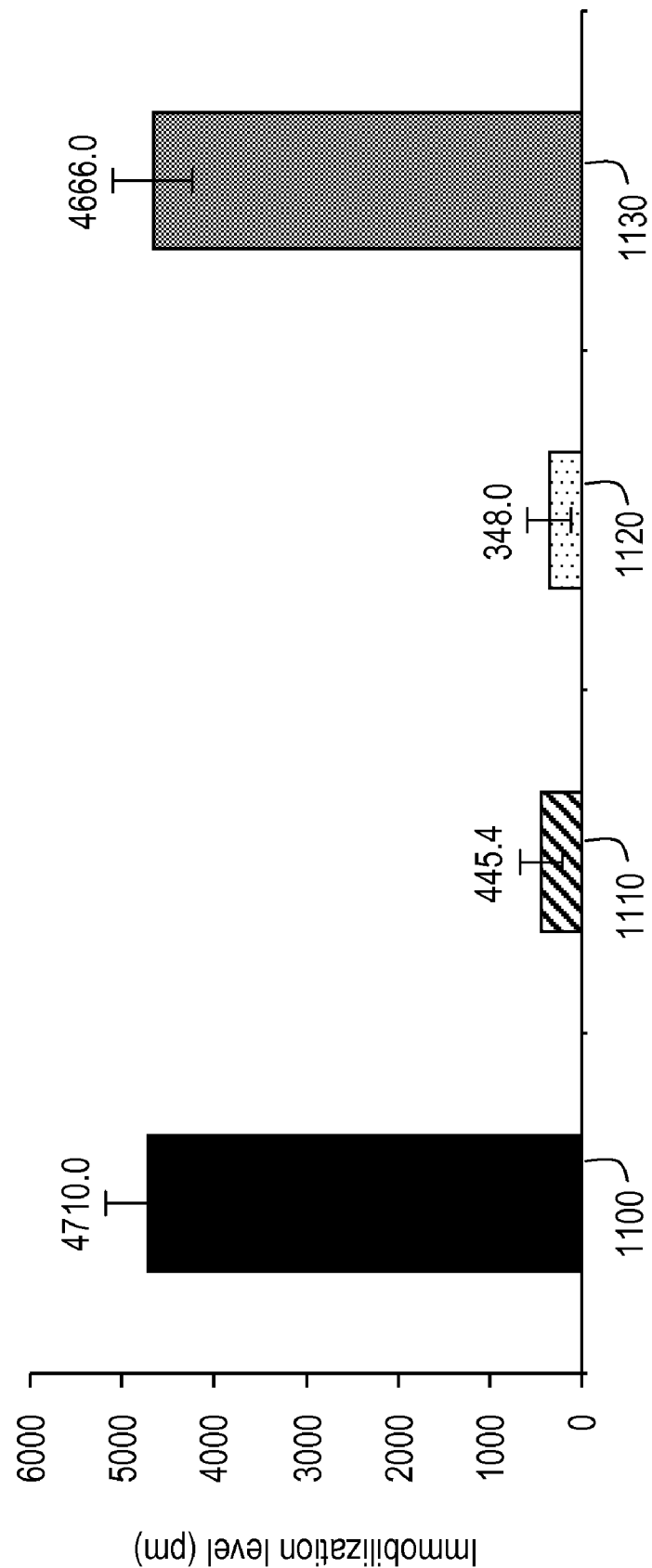
FIG. 11 shows a comparison of CAII or His-tag CAII immobilization levels on the affinity/covalent surface of Example 6, in embodiments of the disclosure.

FIG. 11 shows a comparison of CAII (i.e., CA2) or His-tag CAII immobilization levels on the affinity/covalent surface of Example 6 (1100 his-tag CA2 in acetate; 1110 $CA_2$ in acetate; 1120 CA2 in HEPES plus salt; 1130 his-tag CA2 in HEPES plus salt).

Figure 12:
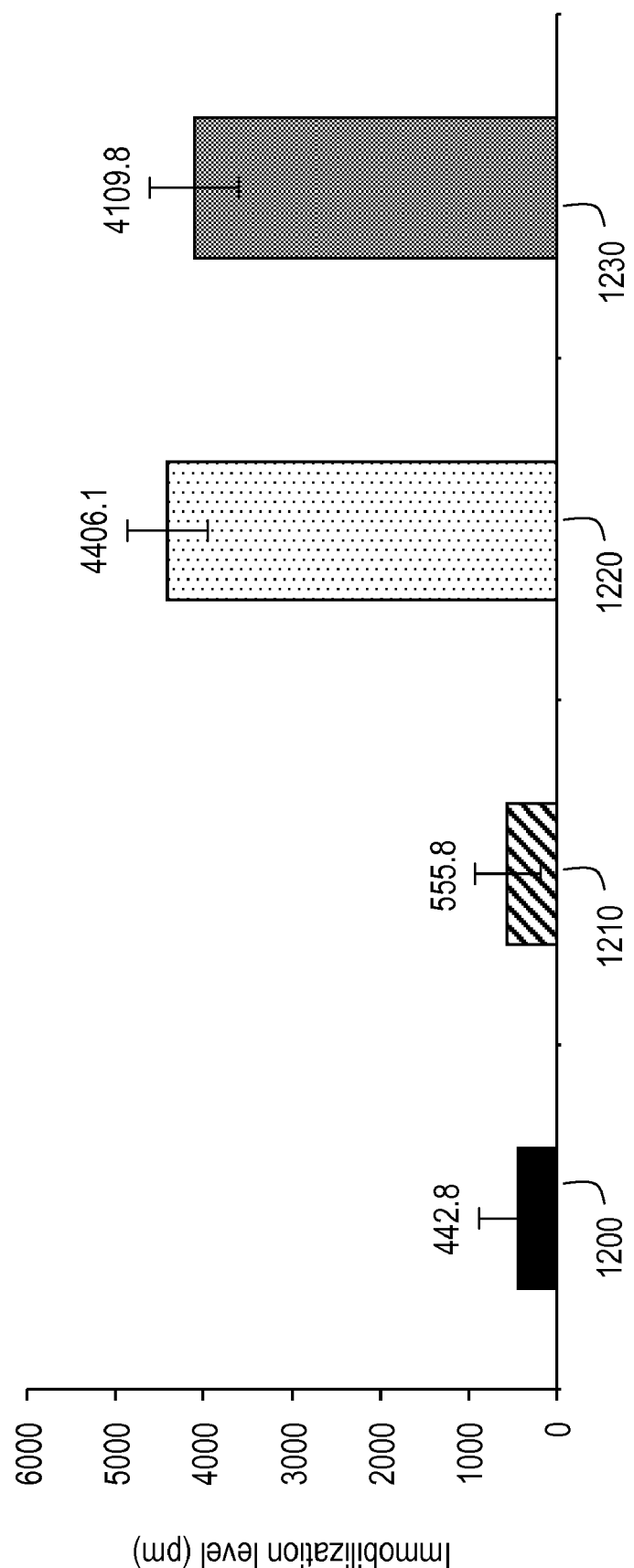
FIG. 12 shows His-tag CAII immobilization levels on the affinity/covalent surface of Example 7 with or without nickel ion treatment, in embodiments of the disclosure.

FIG. 12 shows His-tag CAII immobilization levels on the affinity/covalent surface of Example 7 (1200 EMA050NTA in acetate; 1210 EMA050NTA in HEPES plus salt; 1220 EMA050NTA+Ni ion in acetate; 1230 EMA050NTA+Ni ion in HEPES plus salt) with or without nickel ion treatment.

Figure 13:
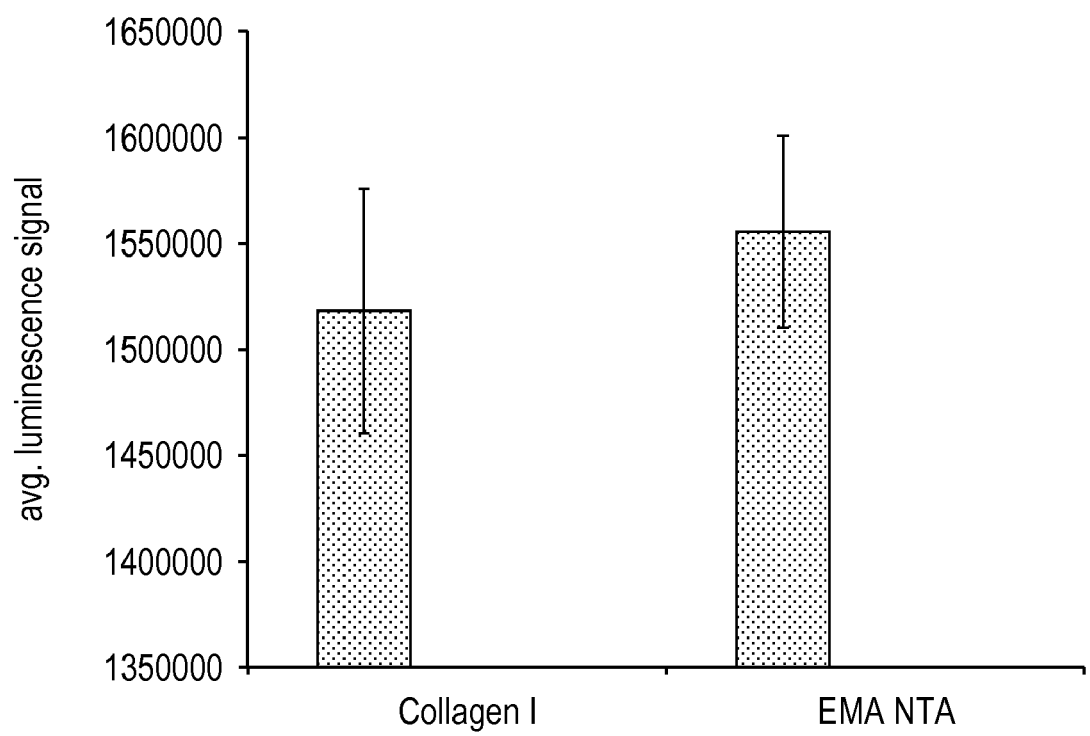
FIG. 13 shows four hour attachment human primary hepatocytes on EMA NTA synthetic surface relative to collagen I.

FIG. 13 shows four hour attachment human primary hepatocytes on EMA NTA synthetic surface (as shown in FIG. 1B) relative to collagen I. The synthetic surface, EMA NTA supports attachment of human primary hepatocytes similar to collagen I in serum culture conditions for 4 hours.

Figure 14:
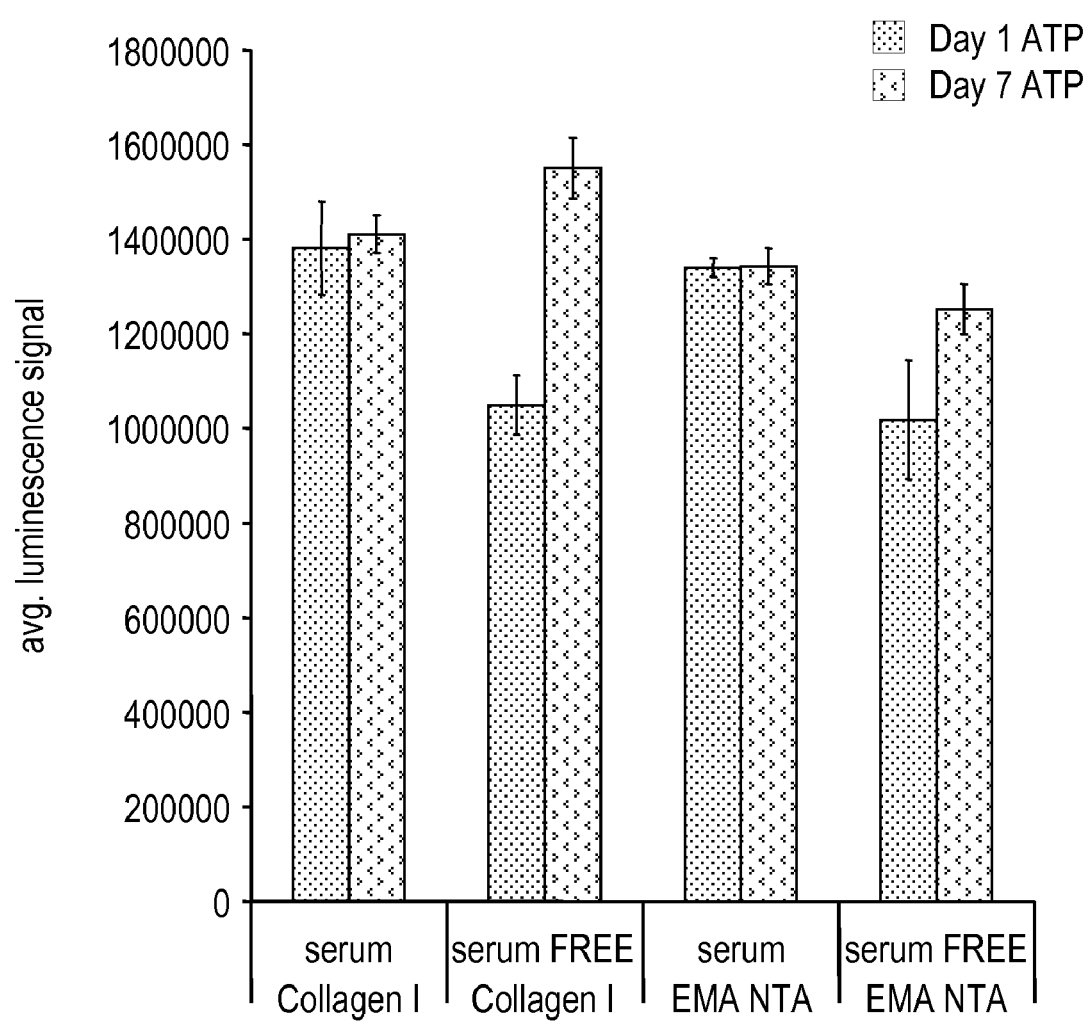
FIG. 14 shows a comparison of attachment (24 h) and retention (7 d) of human primary hepatocytes on EMA NTA synthetic surface relative to collagen I.

FIG. 14 shows a comparison of attachment (24 h) and retention (7 d) of human primary hepatocytes on EMA NTA synthetic surfaces (as shown in FIG. 1B) relative to collagen I; Synthetic EMA NTA surface supports attachment of human primary hepatocytes (with serum and serum free) similar to collagen for 24 hours and 7 days.

FIG. 15 shows relative gene expression of three major metabolism genes (CYP450) in human primary hepatocytes cultured on EMA NTA synthetic surface (as shown in FIG. 1B) relative to collagen I. The synthetic EMA NTA surface shows a functional advantage (increase gene expression) relative to the biological surface, collagen I with serum (industry standard). The serum free condition leads to an elevation of gene expression for CYP2B6 and CYP3A4 on the EMA NTA surfaces.

FIG. 16 shows schematic representations of cells 1710 on a polymer layer 1730 on a substrate 1720 alone and in the presence of a sandwich layer 1740 which may be, for example, protein such as collagen, extracellular matrix, Matrigel™ or a combination. sandwich layer which may be, for example, protein such as collagen, extracellular matrix or Matrigel™ or a combination. Matrigel™ is a tumor cell extract made by BD (Franklin Lakes, N.J.). Extracellular matrix refers to proteins that are present in the extracellular spaces between cells. Extracellular matrix may proteins such as collagen, elastin, fibronectins laminins and glycosaminoglycans.

Figure 16A:
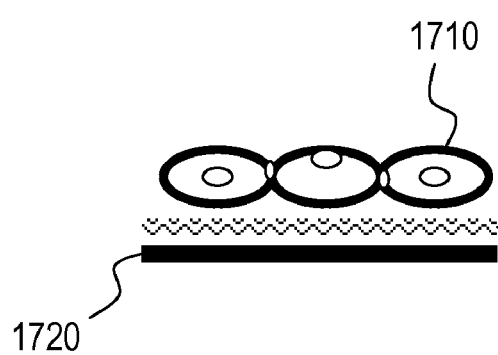
FIG. 16 A-B shows schematic representations of cells on a substrate alone and in the presence of a sandwich layer which may be, for example, collagen or Matrigel™.
Figure 16B:
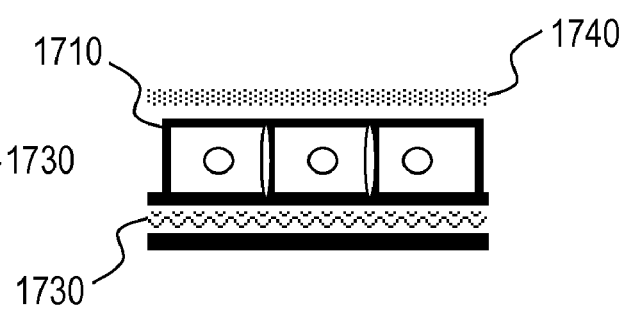
Figure 17A:
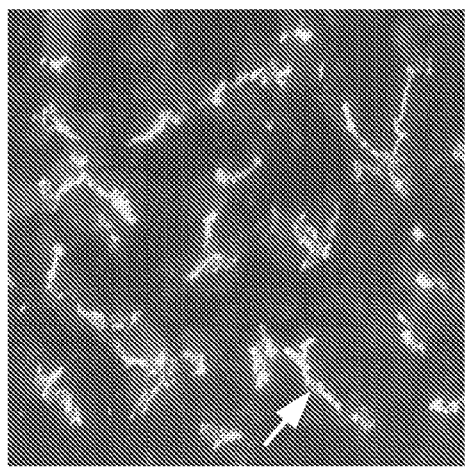
FIG. 17 A-C are micrographs of liver tissue (FIG. 17A), liver cells grown on a collagen I coated substrate (FIG. 17B) and liver cells grown on a collagen I coated substrate, and overlaid with a Matrigel™ sandwich layer (FIG. 17C) fluorescently stained to show MRP2 transporter.
Figure 17B:
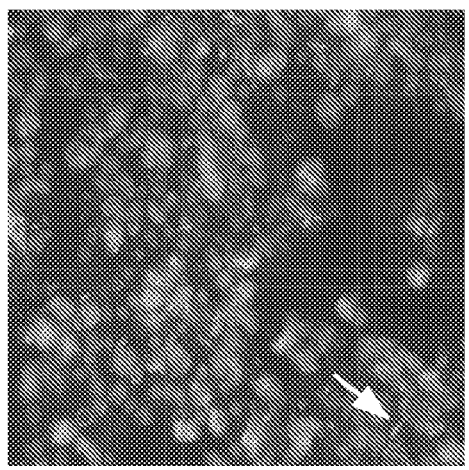
Figure 17C:
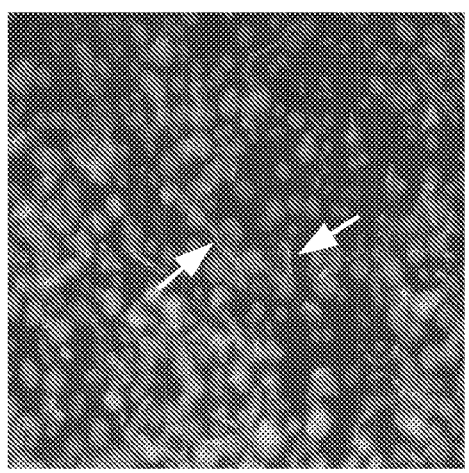

FIG. 17 A-C are micrographs of normal liver tissue (FIG. 17A), liver cells grown on a collagen I coated substrate (FIG. 17B, on a coated substrate as illustrated in FIG. 16A) and liver cells grown on a collagen I coated substrate, and overlaid with a Matrigel™ sandwich layer (FIG. 17C, as illustrated in FIG. 16B) fluorescently stained to show MRP2 transporter. MRP2 transporter is a marker of the bile canaliculi structures at the apical domain between hepatocytes and indicates the degree of restoration of cell membrane polarity. FIG. 17B shows bile canaliculi-like structures that appear like small dots of stain (shown by white arrows). FIG. 17C shows extended and networked bile canaliculi structures (shown by white arrows) indicating good (in vivo like) restoration of cell polarity and a more in vivo-like cell morphology. FIG. 17 shows that these bile canaliculi are present in normal liver tissue, in liver cells grown on a collagen I coated substrate and in liver cells grown on a collagen I coated substrate overlaid with a Matrigel™ sandwich layer.

Figure 18A:
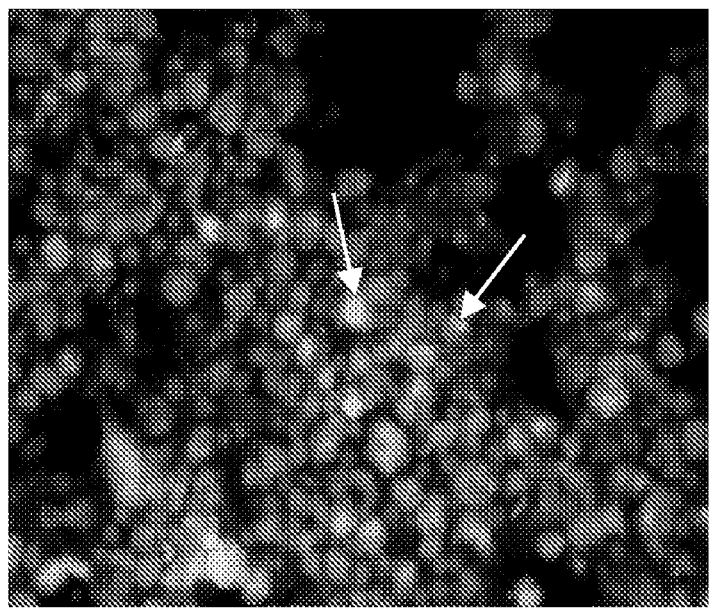
FIGS. 18 (A and B) are micrographs of liver cells grown on synthetic EMA NTA surface alone (FIG. 18A), and in the presence of a Matrigel™ sandwich layer, as illustrated in FIG. 16B.
Figure 18B:
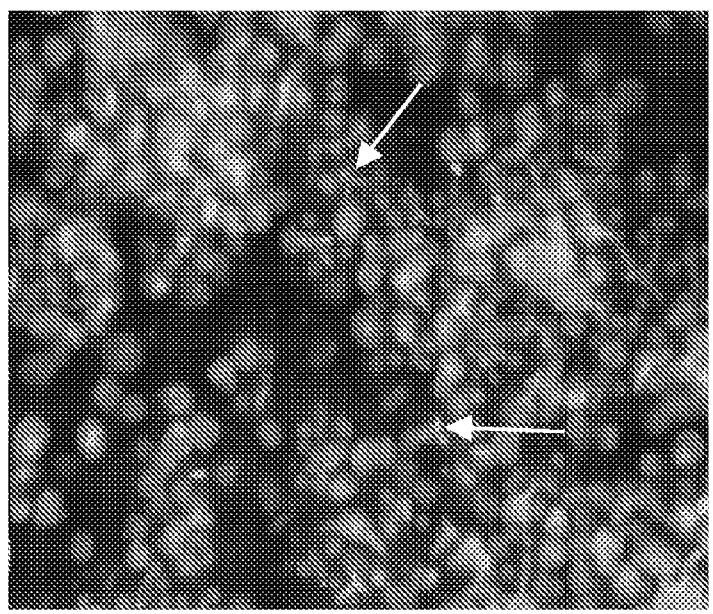

FIGS. 18 (A and B) are micrographs of liver cells grown on synthetic EMA NTA surface alone (FIG. 18A), and in the presence of a Matrigel™ sandwich layer (FIG. 18B) stained to show MRP2 transporter and to show the presence of bile canaliculi structures (indicated by the white arrows). The EMA NTA coated surface shows similar performance to collagen. Without the Matrigel™ overlay (sandwich), bile canaliculi-like structures appear as small dots of stain (shown by white arrow). With the Matrigel™ overlay extended lines of stain (as indicated by white arrows) show restoration of polarity and bile canaliculi structures (in vivo like morphology). Hepatocytes grown on the synthetic EMA NTA surface with the Matrigel™ overlay (sandwich), exhibit hepatocyte polarity. In vivo-like morphology is restored to a greater degree than cells on other experimental surfaces (data not shown).

FIGS. 19 (A and B) are micrographs of liver cells grown on synthetic EMA NTA surface in the presence of a Matrigel™ sandwich in the presence of serum (FIG. 19A) and in the absence of serum (FIG. 19B) stained to show MRP2 transporter. Hepatocyte polarity and morphological markers in serum and serum free culture conditions shows that both conditions support cell culture and the development of bile canaliculi structures. Cells may be distributed more homogeneously across the EMA NTA surfaces in the presence of serum. There may be more crowding and clustering of cells in the serum free condition than in standard culture conditions with serum. Bile canaliculi structures appear to be further extended and more interconnected in the regions where cells are clustered under serum free culture conditions. This may explain the slight increase in function (gene expression) observed in the serum free conditions. FIG. 19 illustrates that the synthetic EMA NTA surface may provide a synthetic surface which can be useful in culturing hepatocytes and other cells in the absence of serum.

EXAMPLES

The following examples serve to more fully describe the manner of using the above-described disclosure, as well as to set forth the best modes contemplated for carrying out various aspects of the disclosure. It is understood that these examples in no way limit the scope of this disclosure, but rather are presented for illustrative purposes. The working examples describe how to prepare and use the LID sensor of the disclosure which are contrasted with the comparative examples.

Example 1

Preparation of EMA-NTA (EMA050NTA) Surface Having Preformed Nanoparticles 0.96 g of ethylene-alt-maleic anhydride copolymer (EMA) was dissolved in 100 mL of anhydrous DMSO under stirring for about 1 hour. To the solution of previously prepared EMA was added 0.92 g of bis-(CML), i.e., N,N'-bis[carboxymethyl]-L-lysine (nitriloacetic acid) (NTA) (available from Aldrich Chemical). The amount of NTA used corresponds to the amount required to convert about 50 mol % of the anhydride groups to NTA groups. The resulting solution was stirred for 48 hours at room temperature. Then, this solution was diluted to about 500 mL with DMSO and then 500 mL anhydrous IPA (50/50 v/v) was added over about 1 hour with stirring to form polymer nanoparticles (EMA050NTA) characterized by dynamic light scattering (DLS) (about 30 nm) and SEM (FIGS. 2B and 2C).

An NTA modified maleic anhydride copolymer (i.e., EMA-NTA), was obtained in Example 1 by reaction of a maleic anhydride polymer, such as ethylene-maleic anhydride copolymer (i.e., EMA), and a reactant having at least one nitriloacetic acid group (such as NTA) and at least one thiol, hydroxyl group or amino group able to react with the anhydride group leading to the formation of the respective ester, thioester, imide or amide groups. The reactant can be selected, for example, from compounds described in EP 0253303B1. A preferred compound is, for example, N",N"-bis[carboxymethyl]-L-lysine (nitriloacetic acid) (NTA), also known as bis-CML, or salts thereof, such as the N,N bis-(Carboxymethyl)-L-Lysine disodium salt mono hydrate. Other names for NTA include, for example, AB-NTA; aminobutyl-NTA; N-(5-Amino-1-carboxypentyl)iminodiacetic acid.

A 5 wt % solution of aminopropylsilane (APS) in DI water was prepared from the 20 wt % commercially available solution. Then, 384-well Epic® insert was dip coated with an aliquot of the APS solution for 10 min. After incubation for 2 to about 24 hours, the APS solution was removed, rinsed three times with water, and three times with anhydrous ethanol, then dried with a stream of nitrogen.

After drying, the APS pre-coated insert was incubated for 10 min. at room temperature in the suspension of EMA050NTA nanoparticles previously prepared. Then, the insert was rinsed with ethanol and was dried by means of a gentle nitrogen stream.

Example 2

SPR Responses on Surfaces with and without Nanoparticle Texture

Coating the EMA050NTA of the disclosure on gold chip: A solution of 3-mercaptopropyl) trimethoxysilane (3-MPT, Aldrich Chemicals) at 20 mM in anhydrous ethanol is added on cleaned gold chip during 2 hours at room temperature. After washing, a solution of 5% aminopropylsilsesquioxane oligomer (APS, Gelest) is added on chip during 15 min at room temperature. Then, the precoated chip was contacted for 10 min at room temperature with EMA polymer in 100% NMP (2D strategy), and another chip was contacted for 10 min at room temperature with a colloidal solution of EMA polymer dispersed NMP/IPA (90/10) (3D strategy). Then, a solution of CML (0.5 g in 10 mL of water) was added onto both chips for 1 hour at room temperature. The addition of a nickel solution was made on Biacore X equipment. His-tag carbonic anhydrase was immobilized on these two surfaces (2D and 3D) at 100 µg/mL in Tris, HCl 20 mM (FIG. 3).

Example 3

SPR Responses Using a Commercially Available NTA Chip Compared with an NTA Nanoparticulate Modified Surface The procedure of Example 2 was repeated to prepare a gold chip with a coating made from colloidal solution of the EMA polymer. Addition of the nickel solution was made in BIACORE X equipment on an experimental chip and on a commercial BIACORE NTA chip. His-tag carbonic anhydrase was immobilized on these two surfaces at 125 µg/mL in Tris, HCl 20 mM (FIG. 4).

Example 4

Epic® Analysis Using an Affinity Surface Only Modification Compared to "Affinity and Covalent" Surface Modification The procedure of Example 1 was repeated to prepare 384-well microplate coated with EMA050NTA. Different approaches were performed on this polymer layer (microplate divided in four areas). Part 1 and part 4 were in contact with a nickel solution. Then, His-tag carbonic anhydrase was immobilized at 50 µg/mL in acetate overnight on both parts. In a second step, after washing, EDC/NHS (200 mM/50 mM) treatment was applied only on part 4. Concerning part 2, EDC/NHS treatment was performed on EMA050NTA before nickel addition. Concerning part 3, nickel addition was made before EDC/NHS treatment. Then, His-tag carbonic anhydrase was immobilized at 50 µg/mL in acetate overnight on parts 2 and 3 (Epic® responses, FIG. 5). Addition of buffer PBS+0.1% DMSO was performed on the immobilized proteins of a first part of the microplate and protein leaching was measured on Epic® equipment (FIG. 6). On another part of the microplate, furosemide ligand was added at 10 µM in PBS and 0.1% DMSO on immobilized proteins and the binding values were measured with Epic® equipment (FIG. 7). The immobilization of his-tag CA2 was accomplished in two buffers (acetate pH 5.5 or HEPES pH 7.4). Results showed immobilization levels greater than about 5,000 pm (FIG. 5) and binding greater than 25 pm (FIG. 7). The loss of protein was estimated in both instances to be about 3 pm, or less than about 0.1 percent of the immobilized protein.

Example 5

Epic® Analysis Using a Known "Affinity and Covalent" Approach Compared to the Present Disclosure The procedure in Example 1 was repeated to prepare 384-well microplate coated with EMA050NTA nanoparticulates. After addition of the nickel solution, His-tag carbonic anhydrase was immobilized at 50 µg/mL either in acetate buffer or in HEPES and salt (i.e., 150 mM NaCl) buffer overnight on inserts. After washing, an EDC/NHS treatment (200 mM/50 mM) was performed during 30 mM in water, protein immobilization levels were obtained using Epic® equipment (FIG. 8). Addition of buffer (PBS and 0.1% DMSO) was performed on immobilized proteins of a part of microplate and protein leaching was measured on Epic® equipment (FIG. 9). On the other part of the microplate, furosemide ligand was added at 10 µM in PBS and 0.1% DMSO on immobilized proteins and binding values were measured with Epic® equipment (FIG. 10).

Example 6

CAII or His-Tag CAII Immobilization Level on Affinity Surface

The procedure of Example 1 was repeated to prepare a 384-well microplate coated with EMA-NTA nanoparticulates. After addition of the nickel solution, His-tag carbonic anhydrase and non-tagged carbonic anhydrase were immobilized at 50 µg/mL in either acetate or in HEPES and 150 mM NaCl buffers overnight on inserts. After washing, an EDC/NHS treatment (200 mM/50 mM) was performed over 30 min in water, and immobilization levels were obtained using Epic® equipment (FIG. 11).

Example 7

His-Tag CAII Immobilization on Affinity Surface with and without Nickel Treatment The procedure of Example 1 was repeated to prepare a 384-well microplate coated with EMANTA nanoparticulates. Addition of the nickel solution was perforated only on half of the microplate. His-tag carbonic anhydrase was then immobilized at 50 µg/mL, in either acetate buffer alone or in HEPES and 150 mM NaCl buffer overnight on each part of the inserts. After washing, an EDC/NHS treatment (200 mM/50 mM) was performed over 30 min in water and immobilization levels were obtained using Epic® equipment (FIG. 12).

Example 8

Cell Culture

Human primary hepatocytes were plated with serum containing (or serum-free) MFE plating medium (in house media preparation, similar to media commercially available from XenoTech) and cultured at 37° C., in a humidified atmosphere of 5% CO2. Cells are maintained in serum-free MFE maintenance medium (in house media preparation, similar to media commercially available from XenoTech) and microscopically observed daily to monitor cell culture health and morphology. Primary hepatocytes were seeded (plated) on the surface at 60,000 cells in 100 uL media per well in 96 well microplate format. Media was replaced daily. HepG2/C3A cells (ATCC #CRL-10741) were cultured in Eagle's Minimum Essential Medium (ATCC #30-2003) optionally supplemented with 10% Fetal Bovine Serum (Invitrogen #16000-077) and 1% Penicillin-Streptomycin (Invitrogen #15140-155). Cells were incubated at 37° C., in 5% CO2 and 95% relative humidity. C3A cells were seeded on the polymer-coated substrates at 5000 cells in 100 uL media per well in 96 well microplate format. Media was replaced daily. Number of cells in culture on EMA NTA surface was quantified using Cell-Glo® Luminescent Cell Viability Assay (Promega G7571). Results are shown in FIGS. 13 and 14.

Example 9

Assessment of Hepatocyte Function Via Gene Expression

After 7 days of culture, cells were lysed to isolate RNA using RNeasy® Mini Kit (Qiagen, Catalog #74106(250), RNase-Free DNase Set (Qiagen, Catalog #79254) and Quant-iT™ RiboGreen® RNA Reagent and Kit (Invitrogen, Catalog #R11490) and the endogenous gene expression of CYP 1A2, 2B6, and 3A4 genes were assessed via Quantitative Real-Time PCR and TaqMan® Low Density Arrays on day 7 of culture, see FIG. 15.

Example 10

Assessment of Morphological Markers

Cell polarity using MRP2 morphological marker for apical domain (bile canaliculi) was assessed at day 7 via immunochemical assays. Fluorescent microscopy was used to image the fluorescently stained markers that indicate the presence of MRP2 in the apical domain as an indication of bile canaliculi structures (FIGS. 17, 18 and 19). A Matrigel™ overlay was added to samples after 1 day in culture to provide a EMA NTA/Matrigel™ sandwich culture configuration and demonstrated extension of bile canaliculi structures as evidence of change in morphology and restoration of membrane polarity. This phenomenon is observed in collagen I/Matrigel™ sandwiches and further demonstrates that the synthetic EMA NTA surface can be used to replace non-synthetic or biological surfaces.

The disclosure has been described with reference to various specific embodiments and techniques. However, it should be understood that many variations and modifications are possible while remaining within the spirit and scope of the disclosure.

What is claimed is:

1. A cell culture article comprising:
a substrate having nanoparticles (NP) on the substrate surface, the nanoparticle comprises:
a polymer of formula (I)

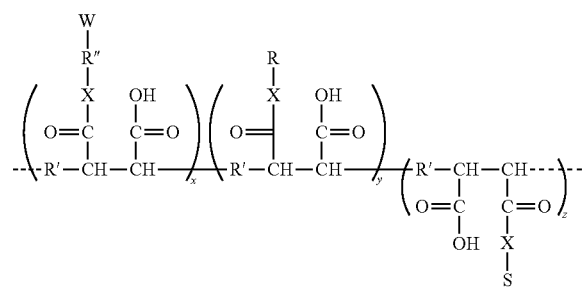

having at least one of: a metal-ion chelating group (x), an ionizable group (y), and a surface substantive group (z), where R is hydrogen or a substituted or unsubstituted, linear or branched, monovalent hydrocarbyl moiety having from 1 to 6 carbon atoms;

R' is a substituted or unsubstituted, linear or branched, divalent hydrocarbyl moiety resulting from copolymerization of an unsaturated monomer having from 2 to 18 carbon atoms with maleic anhydride;

R" is a substituted or unsubstituted, linear or branched, divalent hydrocarbyl moiety having from 1 to 20 carbon atoms;

S comprises at least one point of attachment to the substrate;

W comprises at least one bi-dentate group;

X is an —NH—, —NR—, or O:

the mole ratio of x:(y+z) groups is from about 2:8 to about 8:2, and the nanoparticles have a diameter of from about 10 to about 100 nanometers:

wherein the nanoparticles on the substrate surface comprise a layer having a thickness of from about 20 to about 1,000 nm.

2. A method of culturing cells comprising:
providing a cell culture substrate having nanoparticles (NP) on the substrate surface, the nanoparticle comprises:
a polymer of formula (I)

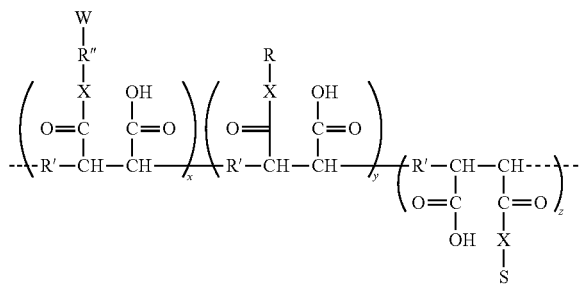

having at least one of: a metal-ion chelating group (x), an ionizable group (y), and a surface substantive group (z), where R is hydrogen or a substituted or unsubstituted, linear or branched, monovalent hydrocarbyl moiety having from 1 to 6 carbon atoms;

R' is a substituted or unsubstituted, linear or branched, divalent hydrocarbyl moiety resulting from copolymerization of an unsaturated monomer having from 2 to 18 carbon atoms with maleic anhydride;

R" is a substituted or unsubstituted, linear or branched, divalent hydrocarbyl moiety having from 1 to 20 carbon atoms;

S comprises at least one point of attachment to the substrate;

W comprises at least one bi-dentate group;

X is an —NH—, —NR—, or O;

the mole ratio of x:(y+z) groups is from about 2:8 to about 8:2; and the nanoparticles have a diameter of from about 10 to about 100 nanometers;

providing cells to the cell culture substrate; and, incubating the cells in a suitable media on the cell culture substrate.

3. A method according to claim 2 further comprising the step of providing a sandwich layer to the cells on the cell culture substrate.

4. The method according to claim 3 wherein the sandwich layer comprises protein.

5. The method according to claim 4 wherein the protein comprises extracellular matrix protein.

6. A method according claim 2 wherein the suitable media comprises serum.

7. A method according claim 2 wherein the cells are hepatocytes.

8. A method according to claim 7 wherein the hepatocytes are primary cells or cell lines.

9. The method according to claim 2 further comprising providing the cell culture substrate on a biosensor for performing biosensor-based label independent cell assays.

10. The method according to claim 3 wherein the suitable media comprises serum.

* * * * *